United States Patent
O'Riordan et al.

(10) Patent No.: US 9,567,382 B2
(45) Date of Patent: Feb. 14, 2017

(54) METHODS TO PRODUCE ROD-DERIVED CONE VIABILITY FACTOR (RDCVF)

(75) Inventors: Catherine R. O'Riordan, Waban, MA (US); William H. Brondyk, Mansfield, MA (US)

(73) Assignee: Genzyme Corporation, Cambridge, MA (US)

(*) Notice: Subject to any disclaimer, the term of this patent is extended or adjusted under 35 U.S.C. 154(b) by 1060 days.

(21) Appl. No.: 12/936,659

(22) PCT Filed: Apr. 15, 2009

(86) PCT No.: PCT/US2009/040645
§ 371 (c)(1),
(2), (4) Date: Oct. 6, 2010

(87) PCT Pub. No.: WO2009/146183
PCT Pub. Date: Dec. 3, 2009

(65) Prior Publication Data
US 2011/0034546 A1   Feb. 10, 2011

Related U.S. Application Data

(60) Provisional application No. 61/045,077, filed on Apr. 15, 2008.

(51) Int. Cl.
*C12N 15/79* (2006.01)
*C07K 14/47* (2006.01)

(52) U.S. Cl.
CPC .................................. *C07K 14/47* (2013.01)

(58) Field of Classification Search
None
See application file for complete search history.

(56) References Cited

U.S. PATENT DOCUMENTS

| 2002/0194643 A1 | 12/2002 | Merot et al. |
| 2004/0204350 A1 | 10/2004 | Leveillard et al. |
| 2005/0107318 A1 | 5/2005 | Wadsworth et al. |
| 2005/0287151 A1* | 12/2005 | Glass .................... 424/178.1 |
| 2007/0166788 A1 | 7/2007 | Jin et al. |

FOREIGN PATENT DOCUMENTS

| EP | 2027889 A1 | 2/2009 |
| WO | WO 03/066810 A2 | 8/2003 |
| WO | WO 2004/108760 | 12/2004 |
| WO | WO 2005/113586 A2 | 12/2005 |

OTHER PUBLICATIONS

Chalmel et al., "Rod-derived Cone Viability Factor-2 is a Novel Bifunctional-thioredoxin-like Protein with Therapeutic Potential," BMC Molecular Biology, 2007, 8:74, 12 pages.
Chen et al., "Isolation and Cloning of Exendin Precursor cDNAs from Single Samples of Venom from the Mexican Beaded Lizard (*Heloderma rorridum*) and the Gila Monster (*Heloderma suspectum*)," Toxicon, Mar. 2006, 47(3):288-295.
Leveillard et al., "Identification and Characterization of Rod-derived Cone Viability Factor," Nature Genetics, (2004), 36(7):755-759.
Martoglio et al., Signal sequences:1-15 more than just greasy peptides, Trends in Cell Biology, vol. 8, No. 10, Oct. 1, 1998, pp. 410-415.

* cited by examiner

*Primary Examiner* — Michael Burkhart
(74) *Attorney, Agent, or Firm* — Roberta L. Robins; Robins Law Group

(57) ABSTRACT

The invention is related to methods of producing rod-derived cone viability factor (RdCVF). This invention also relates to the treatment of an ocular disease in a mammal using RdCVF. Also provided are expression vectors for high secreted expression of RdCVF of using nucleotide sequences encoding heterologous signal proteins and optionally markers for furin cleavage.

16 Claims, 20 Drawing Sheets

Western Blots of CHODXB11 Cells Transiently Transfected with pcDNA-hRdCVF-FL ±Signal Peptides Using anti-hRdCVF-FL 4-12% Bis-Tris, reducing conditions Gel 1
Lane 1: pGZ6 RdCVF SF
Lane 2: pGZ6 RdCVF LF
Lane 5: SeeBlue Plus2 Marker Gel 2
Lane 1: SeeBlue Plus2 Marker
Lane 2: pGZ6 RdCVF SF
Lane 3: pGZ6 RdCVF LF

Figure 5
GUSB signal peptide-FURIN-hRdCVF (Long Form)

A.

MARGSAVAWAALGPLLWGCALG↓LQMPLESGLSSEDSASSESFA*KRIKR*↓MASLFSGR
ILIRNNSDQDELDTEAEVSRRLENRLVLLFFGAGACPQCQAFVPILKDFFVRLTDEFYVL
RAAQLALVYVSQDSTEEQQDLFLKDMPKKWLFLPFEDDLRRDLGRQFSVERLPAVVVL
KPDGDVLTRDGADEIQRLGTACFANWQEAAEVLDRNFQLPEDLEDQEPRSLTECLRRH
KYRVEKAARGGRDPGGGGGEEGGAGGLF (SEQ ID NO:6)

B.

gaattcctccggggaccacacgccgcgctgtccccagcacttaccatggcccgggggtcggcggttgcctgggcggcgctcgggccgtt
gttgtggggctgcgcgctggggctgcagatgcccctcgagtccggcttgctgtcctccgaggactccgccagctccgagagcttcgccaa
gcgcatcaagcgcatggcctccctgttctctggccgcatcctgatccgcaacaatagcgaccaggacgagctggatacggaggctgaggt
cagtcgcaggctggagaaccggctggtgctgctgttctttggtgctggggcttgtccacagtgccaggccttcgtgccatcctcaaggact
tcttcgtgcggctcacagatgagttctatgtactgcgggcggctcagctggccctggtgtacgtgtcccaggactccacggaggagcagca
ggacctgttcctcaaggacatgccaaagaaatggcttttcctgccctttgaggatgatctgaggagggacctcgggcgccagttctcagtgg
agcgcctgccggcggtcgtggtgctcaagccggacggggacgtgctcactcgcgacggcgccgacgagatccagcgcctgggcacc
gcctgcttcgccaactggcaggaggcggccgaggtgctggaccgcaacttccagctgccagaggacctggaggaccaggagccacgg
agcctcaccgagtgcctgcgccgccacaagtaccgcgtggaaaaggcggcgcgaggcgggcgcgacccggggggagggggtggg
gaggagggcggggccggggggctgttctgacccgctagggtggaggagaggagtgggggtttgttgatgaacctccaccccaccccac
ccccgcacgcctgtaatcccagcacttggggaggccaaggcgggaggatcgcttgagcccagaggttcgagatcaacctgggcaagag
agtgagaccctgactctacgaaaattaaaagttagcccggtgtggtggcgcgcacctgtggcttagctaccctgaaaaaaaaaaaaaaaaa
aaaaaaaaaaaaaaaaaaaaaaaaaagcttcc (SEQ ID NO:7)

Figure 6
BDNF signal peptide-FURIN-hRdCVF (Long Form)

A.
MTILFLTMVISYFGCMKA↓AP*MPLESGLSSEDSASSESFA*KRIKR↓MASLFSGRILIRNNS
DQDELDTEAEVSRRLENRLVLLFFGAGACPQCQAFVPILKDFFVRLTDEFYVLRAAQLA
LVYVSQDSTEEQQDLFLKDMPKKWLFLPFEDDLRRDLGRQFSVERLPAVVVLKPDGDV
LTRDGADEIQRLTACFANWQEAAEVLDRNFQLPEDLEDQEPRSLTECLRRHKYRVEKA
ARGGRDPGGGGGEEGGAGGLF (SEQ ID NO:8)

B.
gaattcctccggggaccacacgccgcgctgtccccagcacttaccatgaccatccttttccttactatggttatttcatactttggttgcatgaag
gctgcccccatgcccctcgagtccggcctgtcctccgaggactccgccagctccgagagcttcgccaagcgcatcaagcgcatggcctc
cctgttctctggccgcatcctgatccgcaacaatagcgaccaggacgagctggatacggaggctgaggtcagtcgcaggctggagaacc
ggctggtgctgctgttctttggtgctggggcttgtccacagtgccaggccttcgtgcccatcctcaaggacttcttcgtgcggctcacagatg
agttctatgtactgcgggcggctcagctggccctggtgtacgtgtcccaggactccacggaggagcagcaggacctgttcctcaaggaca
tgccaaagaaatggcttttcctgcccttttgaggatgatctgaggagggacctcgggcgccagttctcagtggagcgcctgccggcggtcgt
ggtgctcaagccggacggggacgtgctcactcgcgacggcgccgacgagatccagcgcctgggcaccgcctgcttcgccaactggca
ggaggcggccgaggtgctggaccgcaacttccagctgccagaggacctggaggaccaggagccacggagcctcaccgagtgcctgc
gccgccacaagtaccgcgtggaaaaggcggcgcgaggcgggcgcgaccccggggagggggtggggaggagggcggggccgg
ggggctgttctgacccgctagggtggaggagaggagtggggtttgttgatgaacctccaccccacccccacccccgcacgcctgtaatcc
cagcacttggggaggccaaggcgggaggatcgcttgagcccagaggttcgagatcaacctgggcaagagagtgagaccctgactctac
gaaaattaaaagttagcccggtgtggtggcgcgcacctgtggcttagctaccctgaaaaaaaaaaaaaaaaaaaaaaaaaaaaaaaaaa
aaaaaaaagcttg (SEQ ID NO:9)

Figure 7
IGF-1 signal peptide-FURIN-hRdCVF (Long Form)

A.
MGKISSLPTQLFKCCFCDFLKVKMHTMSSSHLFYLALCLLTFTSSATA↓GP*MPLESG LSSEDSASSESFAKRIKR*↓MASLFSGRILIRNNSDQDELDTEAEVSRRLENRLVLLFFGAGA CPQCQAFVPILKDFFVRLTDEFYVLRAAQLALVYVSQDSTEEQQDLFLKDMPKKWLFL PFEDDLRRDLGRQFSVERLPAVVVLKPDGDVLTRDGADEIQRLGTACFANWQEAAEVL DRNFQLPEDLEDQEPRSLTECLRRHKYRVEKAARGGRDPGGGGEEGGAGGLF (SEQ ID NO:10)

B.
gaattcctccggggaccacacgccgcgctgtccccagcacttaccatgggaaaaatcagcagtcttccaacccaattatttaagtgctgcttt
tgtgatttcttgaaggtgaagatgcacaccatgtcctcctcgcatctcttctacctggcgctgtgcctgctcaccttcaccagctctgccacggc
tggaccggagatgcccctcgagtccggcctgtcctccgaggactccgccagctccgagagcttcgccaagcgcatcaagcgcatggcct
ccctgttctctggccgcatcctgatccgcaacaatagcgaccaggacgagctggatacggaggctgaggtcagtcgcaggctggagaac
cggctggtgctgctgttctttggtgctggggcttgtccacagtgccaggccttcgtgcccatcctcaaggacttcttcgtgcggctcacagat
gagttctatgtactgcgggcggctcagctggccctggtgtacgtgtcccaggactccacggaggagcagcaggacctgttcctcaaggac
atgccaaagaaatggctttcctgcccttggaggatgatctgaggagggacctcgggcgccagttctcagtggagcgcctgccggcggtcg
tggtgctcaagccggacggggacgtgctcactcgcgacggcgccgacgagatccagcgcctgggcaccgcctgcttcgccaactggca
ggaggcggccgaggtgctggaccgcaacttccagctgccagaggacctggaggaccaggagccacggagcctcaccgagtcctgc
gccgccacaagtaccgcgtggaaaaggcggcgcgaggcgggcgcgaccccggggggagggggtggggaggagggcggggccgg
ggggctgttctgacccgctagggtggaggagaggagtggggtttgttgatgaacctccaccccaccccaccccgcacgcctgtaatcc
cagcacttggggaggccaaggcgggaggatcgcttgagcccagaggttcgagatcaacctgggcaagagagtgagaccctgactctac
gaaaattaaaagttagcccggtgtggtggcgcgcacctgtggcttagctaccctgaaaaaaaaaaaaaaaaaaaaaaaaaaaaaaaaaaa
aaaaaaaagcttc (SEQ ID NO:11)

Figure 8
GUSB signal peptide – Furin - hRdCVF (Short Form)

A.
MARGSAVAWAALGPLLWGCALG↓LQMPLESGLSSEDSASSESFA*KRIKR*↓MASLFSGR
ILIRNNSDQDELDTEAEVSRRLENRLVLLFFGAGACPQCQAFVPILKDFFVRLTDEFYVL
RAAQLALVYVSQDSTEEQQDLFLKDMPKKWLFLPFEDDLRR (SEQ ID NO:12)

B.
gaattcctccggggaccacacgccgcgctgtccccagcacttaccatggcccgggggtcggcggttgcctgggcggcgctcgggccgtt
gttgtggggctgcgcgctggggctgcagatgcccctcgagtccggcttgctgtcctccgaggactccgccagctccgagagcttcgccaa
gcgcatcaagcgcatggcctccctgttctctggccgcatcctgatccgcaacaatagcgaccaggacgagctggatacggaggctgaggt
cagtcgcaggctggagaaccggctggtgctgctgttctttggtgctggggcttgtccacagtgccaggccttcgtgcccatcctcaaggact
tcttcgtgcggctcacagatgagttctatgtactgcgggcggctcagctggccctggtgtacgtgtcccaggactccacggaggagcagca
ggacctgttcctcaaggacatgccaaagaaatggctttcctgcccctttgaggatgatctgaggaggtgaggccccagggaagaccaggg
agggcttcctggagaaggcatttccctggaggtttactgtcctggtactacttgtgcataaagaggtaaagctt (SEQ ID NO:13)

Figure 9
BDNF signal peptide -Furin-hRdCVF (Short Form)

A.

MTILFLTMVISYFGCMKA↓AP<u>MPLESGLSSEDSASSESFA*KRIKR*</u>↓MASLFSGRILIRNNS
DQDELDTEAEVSRRLENRLVLLFFGAGACPQCQAFVPILKDFFVRLTDEFYVLRAAQLA
LVYVSQDSTEEQQDLFLKDMPKKWLFLPFEDDLRR (SEQ ID NO:14)

B.
gaattcctccggggaccacacgccgcgctgtccccagcacttaccatgaccatccttttccttactatggttatttcatactttggttgcatgaag
gctgcccccatgcccctcgagtccggcctgtcctccgaggactccgccagctccgagagcttcgccaagcgcatcaagcgcatggcctc
cctgttctctggccgcatcctgatccgcaacaatagcgaccaggacgagctggatacggaggctgaggtcagtcgcaggctggagaacc
ggctggtgctgctgttctttggtgctggggcttgtccacagtgccaggccttcgtgcccatcctcaaggacttcttcgtgcggctcacagatg
agttctatgtactgcgggcggctcagctggccctggtgtacgtgtcccaggactccacggaggagcagcaggacctgttcctcaaggaca
tgccaaagaaatggctttcctgcccctttgaggatgatctgaggaggtgaggccccagggaagaccagggagggcttcctggagaaggc
atttccctggaggtttactgtcctggtactacttgtgcataaagaggtaaagctt (SEQ ID NO:15)

Figure 10
IGF1signal peptide- Furin- hRdCVF (Short Form)

A.
MGKISSLPTQLFKCCFCDFLKVKMHTMSSSHLFYLALCLLTFTSSATA↓GPMPLESGLSS
EDSASSESFA*KRIKR*↓MASLFSGRILIRNNSDQDELDTEAEVSRRLENRLVLLFFGAGACP
QCQAFVPILKDFFVRLTDEFYVLRAAQLALVYVSQDSTEEQQDLFLKDMPKKWLFLPFE
DDLRR (SEQ ID NO:16)

B.
gaattcctccggggaccacacgccgcgctgtccccagcacttaccatgggaaaaatcagcagtcttccaacccaattatttaagtgctgcttt
tgtgatttcttgaaggtgaagatgcacaccatgtcctcctcgcatctcttctacctggcgctgtgcctgctcaccttcaccagctctgccacggc
tggaccggagatgcccctcgagtccggcctgtcctccgaggactccgccagctccgagagcttcgccaagcgcatcaagcgcatggcct
ccctgttctctggccgcatcctgatccgcaacaatagcgaccaggacgagctggatacggaggctgaggtcagtcgcaggctggagaac
cggctggtgctgctgttctttggtgctggggcttgtccacagtgccaggccttcgtgcccatcctcaaggacttcttcgtgcggctcacagat
gagttctatgtactgcgggcggctcagctggccctggtgtacgtgtccaggactccacggaggagcagcaggacctgttcctcaaggac
atgccaaagaaatggcttttcctgcccttgaggatgatctgaggaggtgaggcccagggaagaccagggagggcttcctggagaagg
catttccctggaggtttactgtcctggtactacttgtgcataaagaggtaaagctt. (SEQ ID NO:17)

Figure 11
HGH Signal Peptide Long Form hRdCVF

A.
ATGGCTACAGGCTCCCGGACGTCCCTGCTCCTGGCTTTTGGCCTGCTCTGCCT
CCCCTGGCTTCAAGAGGGATCCGCC̲G̲CCTCCCTGTTCTCTGGCCGCATCCTGATC
CGCAACAATAGCGACCAGGACGAGCTGGATACGGAGGCTGAGGTCAGTCGCAGGC
TGGAGAACCGGCTGGTGCTGCTGTTCTTTGGTGCTGGGGCTTGTCCACAGTGCCAGG
CCTTCGTGCCCATCCTCAAGGACTTCTTCGTGCGGCTCACAGATGAGTTCTATGTAC
TGCGGGCGGCTCAGCTGGCCCTGGTGTACGTGTCCCAGGACTCCACGGAGGAGCAG
CAGGACCTGTTCCTCAAGGACATGCCAAAGAAATGGCTTTTCCTGCCCTTTGAGGAT
GATCTGAGGAGGGACCTCGGGCGCCAGTTCTCAGTGGAGCGCCTGCCGGCGGTCGT
GGTGCTCAAGCCGGACGGGGACGTGCTCACTCGCGACGGCGCCGACGAGATCCAGC
GCCTGGGCACCGCCTGCTTCGCCAACTGGCAGGAGGCGGCCGAGGTGCTGGACCGC
AACTTCCAGCTGCCAGAGGACCTGGAGGACCAGGAGCCACGGAGCCTCACCGAGTG
CCTGCGCCGCCACAAGTACCGCGTGGAAAAGGCGGCGCGAGGCGGGCGCGACCCC
GGGGGAGGGGGTGGGGAGGAGGGCGGGGCCGGGGGGCTGTTCTGA (SEQ ID NO:18)

B.
ASLFSGRILIRNNSDQDELDTEAEVSRRLENRLVLLFFGAGACPQCQAFVPILKDFFVRLT
DEYVLRAAQLALVYVSQDSTEEQQDLFLKDMPKKWLFLPFEDDLRRDLGRQFSVERLP
AVVVLKPDGDVLTRDGADEIQRLGTACFANWQEAAEVLDRNFQLPEDLEDQEPRSLTE
CLRRHKYRVEKAARGGRDPGGGGEEGGAGGLF (SEQ ID NO:19)

Figure 12
HGH Signal Peptide Short Form hRdCVF

A.
ATGGCTACAGGCTCCCGGACGTCCCTGCTCCTGGCTTTTGGCCTGCTCTGCCT
CCCCTGGCTTCAAGAGGGATCCGCC̲G̲CCTCCCTGTTCTCTGGCCGCATCCTGATC
CGCAACAATAGCGACCAGGACGAGCTGGATACGGAGGCTGAGGTCAGTCGCAGGC
TGGAGAACCGGCTGGTGCTGCTGTTCTTTGGTGCTGGGGCTTGTCCACAGTGCCAGG
CCTTCGTGCCCATCCTCAAGGACTTCTTCGTGCGGCTCACAGATGAGTTCTATGTAC
TGCGGGCGGCTCAGCTGGCCCTGGTGTACGTGTCCCAGGACTCCACGGAGGAGCAG
CAGGACCTGTTCCTCAAGGACATGCCAAAGAAATGGCTTTTCCTGCCCTTTGAGGAT
GATCTGAGGAGGTGA (SEQ ID NO:20)

B.
A̲SLFSGRILIRNNSDQDELDTEAEVSRRLENRLVLLFFGAGACPQCQAFVPILKDFFVRLT
DEFYLRAAQLALVYVSQDSTEEQQDLFLKDMPKKWLFLPFEDDLRR (SEQ ID NO:21)

Figure 13
HGH Signal Peptide Long Form hRdCVF HPC4 Tag

A.
ATGGCTACAGGCTCCCGGACGTCCCTGCTCCTGGCTTTTGGCCTGCTCTGCCT
CCCCTGGCTTCAAGAGGGATCCGCC<u>C</u>GCCTCCCTGTTCTCTGGCCGCATCCTGATC
CGCAACAATAGCGACCAGGACGAGCTGGATACGGAGGCTGAGGTCAGTCGCAGGC
TGGAGAACCGGCTGGTGCTGCTGTTCTTTGGTGCTGGGGCTTGTCCACAGTGCCAGG
CCTTCGTGCCCATCCTCAAGGACTTCTTCGTGCGGCTCACAGATGAGTTCTATGTAC
TGCGGGCGGCTCAGCTGGCCCTGGTGTACGTGTCCCAGGACTCCACGGAGGAGCAG
CAGGACCTGTTCCTCAAGGACATGCCAAAGAAATGGCTTTTCCTGCCCTTTGAGGAT
GATCTGAGGAGGGACCTCGGGCGCCAGTTCTCAGTGGAGCGCCTGCCGGCGGTCGT
GGTGCTCAAGCCGGACGGGGACGTGCTCACTCGCGACGGCGCCGACGAGATCCAGC
GCCTGGGCACCGCCTGCTTCGCCAACTGGCAGGAGGCGGCCGAGGTGCTGGACCGC
AACTTCCAGCTGCCAGAGGACCTGGAGGACCAGGAGCCACGGAGCCTCACCGAGTG
CCTGCGCCGCCACAAGTACCGCGTGGAAAAGGCGGCGCGAGGCGGGCGCGACCCC
GGGGGAGGGGGTGGGGAGGAGGGCGGGGCCGGGGGGCTGTTC<u>GAAGATCAAGTCG
ATCCACGCCTCATCGATGGCAAA</u>TGA (SEQ ID NO:22)

B.
ASLFSGRILIRNNSDQDELDTEAEVSRRLENRLVLLFFGAGACPQCQAFVPILKDFFVRLT
DEYVLRAAQLALVYVSQDSTEEQQDLFLKDMPKKWLFLPFEDDLRRDLGRQFSVERLP
AVVVLKPDGDVLTRDGADEIQRLGTACFANWQEAAEVLDRNFQLPEDLEDQEPRSLTE
CLRRHKYRVEKAARGGRDPGGGGGEEGGAGGLF<u>EDQVDPRLIDGK</u>. (SEQ ID NO:23)

Figure 14
HGH Signal Peptide SHORT FORM human RdCVF HPC4

A.
ATGGCTACAGGCTCCCGGACGTCCCTGCTCCTGGCTTTTGGCCTGCTCTGCCTCCCCTGGCTTCAAGAGGGA
TCCGCC<u>G</u>CCTCCCTGTTCTCTGGCCGCATCCTGATCCGCAACAATAGCGACCAGGACGAGCTGGATACGGAG
GCTGAGGTCAGTCGCAGGCTGGAGAACCGGCTGGTGCTGCTGTTCTTTGGTGCTGGGGCTTGTCCACAGTGC
CAGGCCTTCGTGCCCATCCTCAAGGACTTCTTCGTGCGGCTCACAGATGAGTTCTATGTACTGCGGGCGGCTC
AGCTGGCCCTGGTGTACGTGTCCCAGGACTCCACGGAGGAGCAGCAGGACCTGTTCCTCAAGGACATGCCAA
AGAAATGGCTTTTCCTGCCCTTTGAGGATGATCTGAGGAGG<u>GAAGATCAAGTCGATCCACGCCTCATCGATGGC
AAA</u>TGA (SEQ ID NO:24)

B.
ASLFSGRILIRNNSDQDELDTEAEVSRRLENRLVLLFFGAGACPQCQAFVPILKDFFVRLT
DEFYLRAAQLALVYVSQDSTEEQQDLFLKDMPKKWLFLPFEDDLRR<u>EDQVDPRLIDGK</u>. (SEQ ID NO:25)

Figure 15 nucleoredoxin-like 1 [Homo sapiens]

```
LOCUS       NP_612463                212 aa            linear   PRI 14-SEP-2008
DEFINITION  nucleoredoxin-like 1 [Homo sapiens].
ACCESSION   NP_612463
VERSION     NP_612463.1  GI:19923987
DBSOURCE    REFSEQ: accession NM_138454.1
FEATURES             Location/Qualifiers
     source          1..212
                     /organism="Homo sapiens"
                     /db_xref="taxon:9606"
                     /chromosome="19"
                     /map="19p13.11"
     Protein         1..212
                     /product="nucleoredoxin-like 1"
                     /note="rod-derived cone viability factor; thioredoxin-like
                     6"
                     /calculated_mol_wt=23812
     Region          8..153
                     /region_name="TryX_like_RdCVF"
                     /note="Tryparedoxin (TryX)-like family, Rod-derived cone
                     viability factor (RdCVF) subfamily; RdCVF is a thioredoxin
                     (TRX)-like protein specifically expressed in
                     photoreceptors. RdCVF was isolated and identified as a
                     factor that supports cone survival in...; cd03008"
                     /db_xref="CDD:48557"
     Site            order(44,47)
                     /site_type="other"
                     /note="putative catalytic residues"
                     /db_xref="CDD:48557"
     CDS             1..212
                     /gene="NXNL1"
                     /gene_synonym="RDCVF; TXNL6"
                     /coded_by="NM_138454.1:48..686"
                     /db_xref="CCDS:CCDS12360.1"
                     /db_xref="GeneID:115861"
                     /db_xref="HGNC:25179"
                     /db_xref="HPRD:12300"
                     /db_xref="MIM:608791"
ORIGIN
        1 maslfsgril irnnsdqdel dteaevsrrl enrlvllffg agacpqcqaf vpilkdffvr
       61 ltdefyvlra aqlalvyvsq dsteeqqdlf lkdmpkkwlf lpfeddlrrd lgrqfsverl
      121 pavvvlkpdg dvltrdgade iqrlgtacfa nwqeaaevld rnfqlpedle dqeprsltec
      181 lrrhkyrvek aarggrdpgg gggeeggagg lf    (SEQ ID NO. 32)
```

FIGURE 16

Homo sapiens nucleoredoxin-like 1 (NXNL1), mRNA

```
LOCUS       NM_138454                948 bp    mRNA    linear   PRI 14-SEP-2008
DEFINITION  Homo sapiens nucleoredoxin-like 1 (NXNL1), mRNA.
ACCESSION   NM_138454
VERSION     NM_138454.1  GI:19923986
FEATURES             Location/Qualifiers
     source          1..948
                     /organism="Homo sapiens"
                     /mol_type="mRNA"
                     /db_xref="taxon:9606"
                     /chromosome="19"
                     /map="19p13.11"
     gene            1..948
                     /gene="NXNL1"
                     /gene_synonym="RDCVF; TXNL6"
                     /note="nucleoredoxin-like 1"
                     /db_xref="GeneID:115861"
                     /db_xref="HGNC:25179"
                     /db_xref="HPRD:12300"
                     /db_xref="MIM:608791"
     exon            1..373
                     /gene="NXNL1"
                     /gene_synonym="RDCVF; TXNL6"
                     /inference="alignment:Splign"
                     /number=1
     CDS             48..686
                     /gene="NXNL1"
                     /gene_synonym="RDCVF; TXNL6"
                     /note="rod-derived cone viability factor; thioredoxin-like
                     6"
                     /codon_start=1
                     /product="nucleoredoxin-like 1"
                     /protein_id="NP_612463.1"
                     /db_xref="GI:19923987"
                     /db_xref="CCDS:CCDS12360.1"
                     /db_xref="GeneID:115861"
                     /db_xref="HGNC:25179"
                     /db_xref="HPRD:12300"
                     /db_xref="MIM:608791"
                     /translation="MASLFSGRILIRNNSDQDELDTEAEVSRRLENRLVLLFFGAGAC
                     PQCQAFVPILKDFFVRLTDEFYVLRAAQLALVYVSQDSTEEQQDLFLKDMPKKWLFLP
                     FEDDLRRDLGRQFSVERLPAVVVLKPDGDVLTRDGADEIQRLGTACFANWQEAAEVLD
                     RNFQLPEDLEDQEPRSLTECLRRHKYRVEKAARGGRDPGGGGGEEGGAGGLF" (SEQ
ID NO. 32)
     exon            374..908
                     /gene="NXNL1"
                     /gene_synonym="RDCVF; TXNL6"
                     /inference="alignment:Splign"
                     /number=2
ORIGIN
        1 ccggggacca cacgccgcgc tgtccccagc acccaaccca ggttaccatg gcctccctgt
       61 tctctggccg catcctgatc cgcaacaata gcgaccagga cgagctggat acggaggctg
      121 aggtcagtcg caggctggag aaccggctgg tgctgctgtt ctttggtgct ggggcttgtc
      181 cacagtgcca ggccttcgtg cccatcctca aggacttctt cgtgcggctc acagatgagt
      241 tctatgtact gcgggcggct cagctggccc tggtgtacgt gtcccaggac tccacggagg
      301 agcagcagga cctgttcctc aaggacatgc caaagaaatg gcttttcctg ccctttgagg
      361 atgatctgag gagggacctc gggcgccagt tctcagtgga gcgcctgccg gcggtcgtgg
```

FIGURE 16 (CONT.)

```
421 tgctcaagcc ggacggggac gtgctcactc gcgacggcgc cgacgagatc cagcgcctgg
481 gcaccgcctg cttcgccaac tggcaggagg cggccgaggt gctggaccgc aacttccagc
541 tgccagagga cctggaggac caggagccac ggagcctcac cgagtgcctg cgccgccaca
601 agtaccgcgt ggaaaaggcg gcgcgaggcg ggcgcgaccc cggggggaggg ggtggggagg
661 agggcggggc cggggggctg ttctgacccg ctagggtgga ggagaggagt ggggtttgtt
721 gatgaacctc cacccccacc ccaccccgc acgcctgtaa tcccagcact tggggaggcc
781 aaggcgggag gatcgcttga gcccagaggt tcgagatcaa cctgggcaag agagtgagac
841 cctgactcta cgaaaattaa aagttagccc ggtgtggtgg cgcgcacctg tggcttagct
901 accctgaaaa aaaaaaaaaa aaaaaaaaaa aaaaaaaaaa aaaaaaaa (SEQ ID NO. 33)
```

SIGNAL PEPTIDES

FIGURE 17 (CONT.)
Prepillin like signal
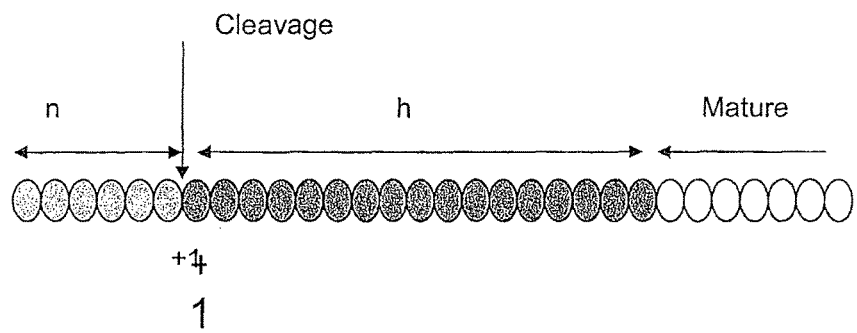
Bacterioicin Signal
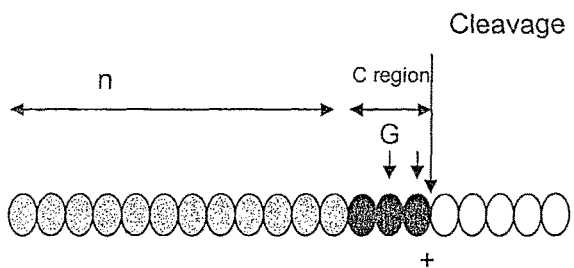
All white circles are part of the mature protein
+1 indicates the first position of the mature protein

METHODS TO PRODUCE ROD-DERIVED CONE VIABILITY FACTOR (RDCVF)

This application is a §371 filing from of PCT/US2009/040645, filed Apr. 15, 2009, and claims the benefit under 35 U.S.C. §119(e)(1) of U.S. Provisional Application Ser. No. 61/045,077, filed Apr. 15, 2008, which applications are incorporated herein by reference in their entireties and from which applications priority is claimed pursuant to the provisions of 35 U.S.C. §§119/120.

TECHNICAL FIELD

This invention relates to methods of producing rod-derived cone viability factor (RdCVF) using engineered cells. This invention also relates to the treatment of an ocular disease in a mammal using RdCVF. The invention further concerns the cells and the expression vectors that are used to secrete RdCVF.

BACKGROUND

Retinitis pigmentosa is an untreatable, inherited retinal disease that leads to blindness. The disease initiates with the loss of night vision due to rod photoreceptor degeneration, followed by irreversible progressive loss of cone photoreceptors. Although loss of rods has substantial functional consequences such as night blindness and some constriction of visual fields, rod death by itself does not cause severe vision loss. Rather, it is the delayed wave of non-autonomous cone photoreceptor degeneration that results in blindness.

It has previously been shown that factors secreted from rods are essential for cone viability. One such trophic factor, RdCVF, has been identified (see U.S. Pub. No. 2004/0204350, Channel et al., BMC Molecular Biology 2007, 8:74; Leveillard et al., 2004, Nature Genetics, 36: 755-759; and Leveillard et al. at http://www.hal.inserm.fr/docs/00/31/23/78/DOC/Manuscript_on_April_15.doc). The feasibility of delivering RdCVF to the retina of a mouse model of retinitis pigmentosa (rd1) using recombinant AAV vectors has been evaluated. In vivo results suggests that efficient delivery of vector derived RdCVF protein to target photoreceptor cells requires novel secreted versions of the protein by the addition of specific signal peptides. Therapeutic applications of RdCVF have been explored, e.g., see WO 03/066810A2, EP 2027889A1, WO 2005/113586A2, Purification of secreted RdCVF and subsequent biochemical analysis confirms that RdCVF(LF) has anti-oxidative properties.

Recombinant expression of RdCVF at a large scale has been challenging. Effective expression of RdCVF from a gene therapy vector has also been challenging. Without being limited as to theory, it is theorized that post-translational events are largely responsible for the less than optimal levels of protein expression in either recombinant protein expression systems or in expression from a gene therapy vector. Following translation, proteins are routed specifically to secretory or endocytic pathways in the endoplasmic reticulum and traverse the Golgi network. Secreted proteins comprise a signal peptide, which is recognized during translation by the signal recognition pathway. Subsequently, the signal peptide is cleaved by a membrane—bound signal peptidase and the mature secreted protein enters a secretory vesicle. Thus secreted proteins are destined for the secretory pathway by recognition of their N-terminal signal peptides.

The presently disclosed invention seeks to improve RdCVF expression profiles, including improving RdCVF secretion from cells both in vitro and in vivo.

SUMMARY OF THE INVENTION

In one aspect, the invention relates to an expression vector for expression of rod-derived cone viability factor (RdCVF) comprising a) a RdCVF-encoding nucleotide sequence lacking the initiating methionine coding sequence; b) an exogenous signal peptide-encoding nucleotide sequence positioned upstream of the RdCVF-encoding nucleotide sequence, wherein the exogenous signal peptide-encoding sequence is selected from the group consisting of: human growth hormone (hGH), brain-derived neurotrophic factor (BDNF), insulin growth factor-1 (IGF-1), or β-glucoronidase (GUSB).

In one aspect, the invention relates to an expression vector for expression of rod-derived cone viability factor (RdCVF) comprising a) a RdCVF-encoding nucleotide sequence; b) a signal peptide-encoding nucleotide sequence positioned upstream of the RdCVF-encoding nucleotide sequence, wherein the signal peptide-encoding sequence encodes an exogenous signal peptide; and c) a nucleotide sequence encoding a furin cleavage marker located downstream of the signal peptide-encoding nucleotide sequence and upstream of the RdCVF-encoding nucleotide sequence.

The signal peptide-encoding sequence and the furin cleavage marker sequence according to some embodiments may be separated by a sequence encoding an amino acid linker.

In one embodiment, the RdCVF-encoding nucleotide sequence lacks the initiating methionine coding sequence.

The signal peptide—encoding sequence may be that of human growth hormone (hGH), brain-derived neurotrophioc factor (BDNF), insulin growth factor-1 (IGF-1), or β-glucoronidase (GUSB).

In one aspect, the invention relates to an expression vector for high secreted expression of rod-derived cone viability factor (RdCVF) in a cell, said vector comprising a) a signal peptide-encoding nucleotide sequence of a heterologous secreted protein upstream of the N-terminus of a RdCVF-encoding nucleotide sequence, wherein the heterologous secreted protein is human growth hormone (hGH), brain-derived neurotrophic factor (BDNF), Insulin growth factor-1 (IGF-1), or β-glucoronidase (GUSB); b) a RdCVF-encoding nucleotide sequence; and c) optionally a nucleotide sequence encoding for a subtilisin-like serine endoprotease furin cleavage marker located downstream of the signal peptide-encoding nucleotide sequence of (a) and immediately upstream of the sequence encoding the initiating methionine of RdCVF, wherein the signal peptide-encoding sequence (a) and sequence encoding the for a subtilisin-like serine endoprotease furin cleavage marker (c) are separated by a sequence encoding an amino acid linker.

Another aspect of the invention is a method of treating an ocular disease in a mammal using RdCVF. The method comprises administering to a diseased eye of the mammal the chimeric RdCVF fusion protein of the invention at a therapeutically effective amount.

In another aspect, is a method of treating an ocular disease in a mammal using RdCVF wherein the method comprises administering to a diseased eye of the mammal a nucleic acid encoding the RdCVF fusion protein of the invention, where the RdCVF is expressed at a therapeutically effective amount. In certain aspects, the nucleic acid is delivered via a recombinant viral vector, such as an adeno-associated virus (AAV) or an adenovirus (Ad). The viral vector comprises the nucleic acid encoding for rod-derived cone viability factor (RdCVF) wherein the nucleic acid comprises a) a signal peptide-encoding nucleotide sequence of a heterologous secreted protein upstream of the N-terminus of a RdCVF-encoding nucleotide sequence, wherein the heterologous secreted protein is human growth hormone (hGH), brain-derived neurotrophic factor (BDNF), Insulin growth factor-1 (IGF-1), or β-glucoronidase (GUSB); b) a RdCVF-encoding nucleotide sequence; and c) optionally a nucleotide sequence encoding for a subtilisin-like serine endoprotease furin cleavage marker located downstream of the signal peptide-encoding nucleotide sequence of (a) and immediately upstream of the sequence encoding the initiating methionine of RdCVF, wherein the signal peptide-encoding sequence (a) and sequence encoding the for a subtilisin-like serine endoprotease furin cleavage marker (c) are separated by a sequence encoding an amino acid linker. The viral vector may be injected into the eye to produce RdCVF protein intra-ocularly.

In another aspect, the invention relates to a method for producing a recombinant rod-derived cone viability factor (RdCVF) in the eye, said method comprising injecting a recombinant viral vector, e.g AAV or Ad, into the eye, wherein ocular cells are transduced and produce RdCVF. The produced RdCVF may be secreted into the vitreal humor and provide therapeutic effects. The virus may be injected into a subject with retinitis pigmentosa, wherein the secreted RdCVF provides therapeutic effects.

In some embodiments, the cell is a mammalian cell and said mammalian cell is a CHO cell or a COS cell. In some embodiments, the amino acid linker is between 10 and 25 amino acids long. In some embodiments, the amino acid linker is MPLESGLSSEDSASSESFA (SEQ ID NO. 1). In some embodiments, the RdCVF-encoding sequence encodes the long or short form of RdCVF. In some embodiments the heterologous protein is HGH, BDNF, IGF-1 or GUSB. In some embodiments, the nucleotide sequence encoding for a subtilisin-like serine endoprotease furin cleavage marker is a sequence encoding the amino acid sequence KRIKR (SEQ ID NO. 2).

In another aspect, the invention relates to a mammalian cell producing recombinant RdCVF, comprising a vector disclosed herein.

In a another aspect, the invention relates to a method for high secreted expression of rod-derived cone viability factor (RdCVF) in a mammalian cell, said method comprises culturing a cell comprising a chimeric protein expression vector disclosed herein.

In one embodiment, the mammalian cell is a CHO cell or a COS cell.

In a another aspect, the invention relates to a method for producing a recombinant rod-derived cone viability factor (RdCVF), said method comprising growing a cell disclosed herein and isolating the protein produced.

BRIEF DESCRIPTION OF THE DRAWINGS

FIG. 5 shows the nucleic acid sequence (A) and the amino acid sequence (B) of the GUSB signal peptide-furin-hRdCVF Long Form (LF) according to one embodiment.

FIG. 6 shows the nucleic acid sequence (A) and the amino acid sequence (B) of the BDNF signal peptide-furin-hRdCVF Long Form (LF) according to one embodiment.

FIG. 7 shows the nucleic acid sequence (A) and the amino acid sequence (B) of the IGF-1 signal peptide-furin-hRdCVF Long Form (LF) according to one embodiment.

FIG. 8 shows the nucleic acid sequence (A) and the amino acid sequence (B) of the GUSB signal peptide-furin-hRdCVF Short Form (SF) according to one embodiment.

FIG. 9 shows the nucleic acid sequence (A) and the amino acid sequence (B) of the BDNF signal peptide-furin-hRdCVF Short Form (SF) according to one embodiment.

FIG. 10 shows the nucleic acid sequence (A) and the amino acid sequence (B) of the IGF1 signal peptide-furin-hRdCVF Short Form (SF) according to one embodiment.

FIG. 11 shows the nucleic acid sequence (A) and the amino acid sequence (B) of the hGH signal peptide hRdCVF Long Form (LF) according to one embodiment. The predicted amino acid sequence of secreted hRdCVF (LF) is shown, following signal peptidase cleavage of HGH signal peptide is depicted below.

FIG. 12 shows the nucleic acid sequence (A) and the amino acid sequence (B) of the hGH signal peptide hRdCVF Short Form (SF) according to one embodiment. The predicted amino acid sequence of secreted hRdCVF (SF) is shown, following signal peptidase cleavage of HGH signal peptide is depicted below.

FIG. 13 shows the A. nucleic acid sequence and the B. amino acid sequence of the hGH signal peptide hRdCVF (LF) with HPC4 tag according to one embodiment. The predicted amino acid sequence of secreted hRdCVF (Long Form) HPC4 tag is shown, following signal peptidase cleavage of HGH signal peptide is depicted below. The twelve amino acid HPC4 tag is depicted by underline.

FIG. 14 shows the nucleic acid sequence (A) and the amino acid sequence (B) of the hGH signal peptide hRdCVF (SF) with HPC4 tag according to one embodiment. The predicted amino acid sequence of secreted hRdCVF (Short Form) HPC4 tag is shown, following signal peptidase cleavage of HGH signal peptide is depicted below. The sequence for the HPC4 tag is underlined.

FIG. 15 shows an example of RdCVF protein sequence according to one embodiment.

FIG. 16 shows an example of RdCVF nucleotide sequence according to one embodiment.

DETAILED DESCRIPTION OF THE INVENTION

Figure 1:
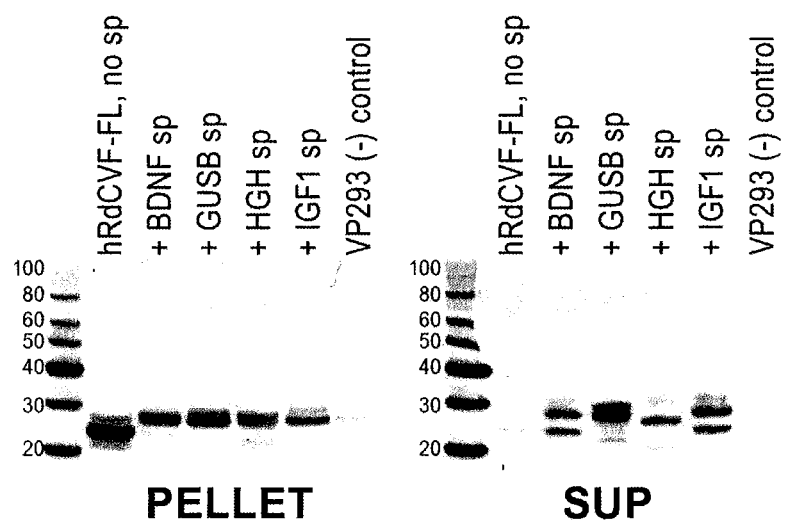
FIG. 1 show Western blots of cells transfected with plasmid encoding for RdCVF and signal peptides according to one embodiment. Immunoblot of cell lysates (Sup) and cell pellet (Pellet) following transfection with plasmid encoding cDNA for RdCVF (LF) with signal peptides from BDNF, GUSB, IGF1 or HGH are indicated in the figure. The immunoblot is probed with an antibody generated against RdCVF (LF). This demonstrates inclusion of a signal peptide in the RdCVF sequence results in successful secretion of RdCVF from cells, as evidenced by the presence of RdCVF in cell supernatants "sup". The pellet fraction represents the fraction of RdCVF that remains intracellular.
Figure 2:
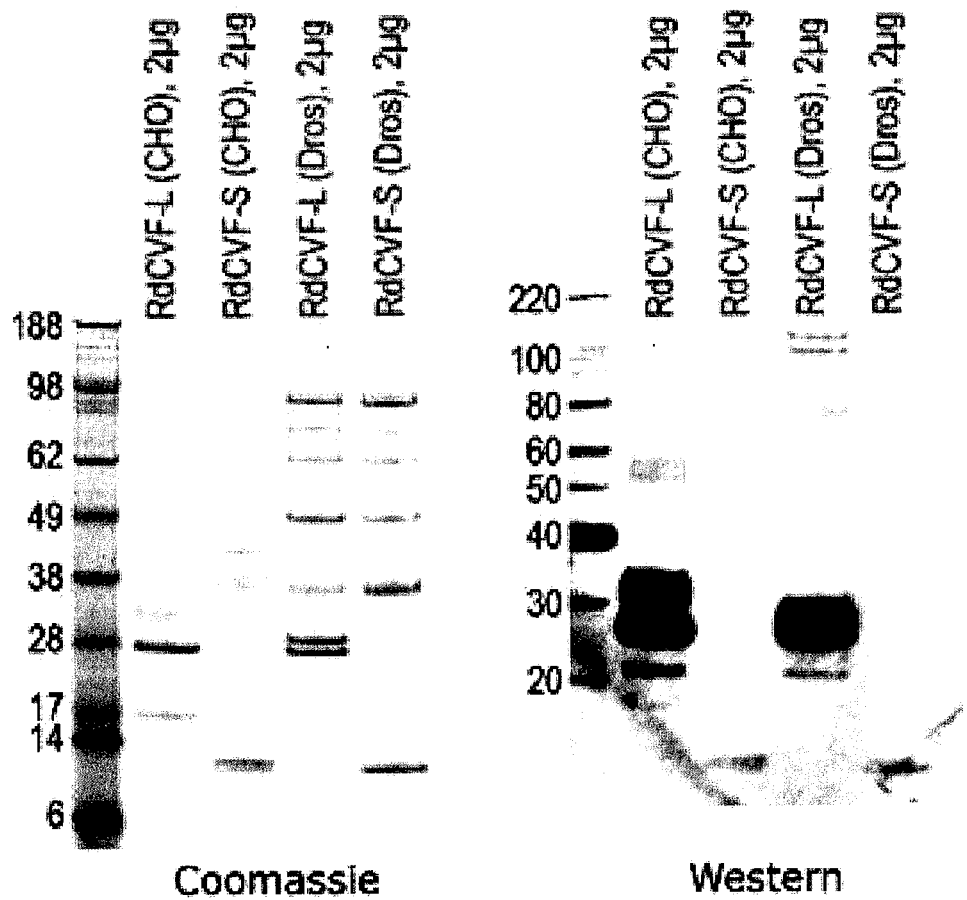
FIG. 2 shows SDS-PAGE analysis of purified RdCVF protein (with affinity tag) produced either in CHO or *Drosophila* cells according to one embodiment. The immunoblot is probed with an antibody against the affinity tag.

The instant invention provides an expression system that provides improved secretion of recombinantly expressed RdCVF, which is poorly secreted in its native form. The invention provides a chimeric protein that can be generated by adding the signal peptide from efficiently secreted proteins to the N terminus of the poorly secreted protein. The resulting chimeric protein will be secreted via the classical secretory pathway. Preferably the chimeric protein further comprises a cleavable linker for separating the signal peptide from the recombinant RdCVF.

The RdCVF gene encodes two products through alternative splicing. The short form RdCVF is a truncated thioredoxin (txn)-like protein specifically expressed by photoreceptors which has been shown to promote cone survival. An alternatively spliced long form of RdCVF is encoding a longer protein with a C-terminal extension and could have oxidoreductase activity. Similar to Txn, RdCVF might be a new example of a bifunctional protein, with the long form having a putative thiol-oxydoreductase activity and the short form having trophic activity for cones but no redox activity. Polypeptide sequences of human RdCVF and nucleic acid sequences encoding such human RdCVF have been reported. Examples of such polypeptide sequences include, but are not limited to, those disclosed in FIG. 15, or homologue or a portion thereof. Examples of such nucleic acid sequences include, but are not limited to, those disclosed in FIG. 16, or homologue or a portion thereof.

Insertion of a signal peptide upstream of the initiating methionine in the chimeric protein often results in inefficient recognition of the signal sequence by its cognate signal peptidase. To overcome this limitation, the codon for the initiating methionine from the cDNA sequence of the chimeric protein may be removed; this generates a final secreted protein product that lacks an initiating methionine. Alternatively, the signal sequence for the subtilisin-like serine endoprotease furin can be inserted downstream of the signal peptide but immediately upstream of the initiating methionine of the chimeric protein. Furin which resides in the trans Golgi network cleaves specifically at the C terminal side of the consensus sequence Arg-X-Lys/Arg-Arg↓-(R X (K/R)R) (SEQ ID NO:3) in the trans Golgi network (TGN). Using this approach the secreted chimeric protein still retains its initiating methionine following processing by both the relevant signal peptidase in the ER and the furin endoprotease in the TGN.

The convention for writing peptide sequences is to put the C-terminal end on the right and write the sequence from N- to C-terminus. Reference to the C terminal is defined as the end of the amino acid chain terminated typically, but not necessarily, by a carboxyl group. Reference to the N terminal is defined as the end of the amino acid chain terminated typically, but not necessarily, by an amino group.

"Amino acid" or "amino acid sequence" as used herein, include references to oligopeptide, peptide, polypeptide, or protein sequence, or to a fragment, portion, or subunit of any of these, and to naturally occurring or synthetic molecules. The terms "polypeptide" and "protein" include amino acids joined to each other by peptide bonds or modified peptide bonds, i.e., peptide isosteres, and may contain modified amino acids other than the 20 gene-encoded amino acids. The term "polypeptide" also includes peptides and polypeptide fragments, motifs and the like.

The terms "polypeptide," "peptide," and "protein" are used interchangeably to refer to polymers of amino acids of any length. Peptides and polypeptides can be either entirely composed of synthetic, non-natural analogues of amino acids, or, is a chimeric molecule of partly natural peptide amino acids and partly non-natural analogs of amino acids.

The terms "transformation" and "transfection" or "transduction" refer to intracellular introduction of a nucleic acid. A nucleic acid can be introduced into a plant or an animal cell or a prokaryotic or eukaryotic cell by a number of methods known in the art or described herein.

The term "isolated" refers to a deoxyribonucleic acid, a ribonucleic acid, or a nucleic acid analog having a polynucleotide sequence that is separated from other nucleic acid sequences in such a way that does not naturally occur. An isolated nucleic acid encompasses nucleic acids that may be partially or wholly chemically or recombinantly synthesized and/or purified by standard techniques known in the art.

The term "variant" refers to a nucleotide sequence that is substantially similar, over the entire length, to another nucleotide sequence. The term "substantially similar" when used herein with respect to a nucleotide sequence means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. In some embodiments, the expression vector comprises variants of the nucleotide sequences disclosed herein.

"Heterologous protein" as used herein, is a protein that is not normally produced by or required for viability of the host organism. This term contemplates the functional insertion of DNA encoding such protein, via recombinant DNA technology, into an expression vehicle. Non-limiting examples of heterologous proteins of this invention include hGH, BDNF, IGF-1, GUSB.

The term "vector" refers to viral or non-viral, prokaryotic or eukaryotic, deoxyribonucleic acid, ribonucleic acid or a nucleic acid analog, that is capable of carrying another nucleic acid. A vector may either carry a nucleic acid into a cell, referred to as "host cell", so that all or a part of the nucleic acid is transcribed or expressed. Alternatively, a vector may be used in an in vitro transcription assay. Vectors are frequently assembled as composites of elements derived from different viral, bacterial, or mammalian genes. Vectors contain various coding and non-coding sequences including sequences coding for selectable markers (e.g., an antibiotic resistance gene), sequences that facilitate their propagation in bacteria, or one or more transcription units that are expressed only in certain cell types. For example, mammalian expression vectors often contain both prokaryotic sequences that facilitate the propagation of the vector in bacteria and one or more eukaryotic transcription units that are expressed only in eukaryotic cells. It will be appreciated by those skilled in the art that the design of the expression vector can depend on such factors as the choice of the host cell to be transformed, the level of expression of protein desired, etc.

Vectors include, for example, plasmids, phagemids, and viral vectors. Vectors that have an existing promoter can be modified by standard recombinant DNA techniques known in the art to replace the promoter with any promoter sequence variation. In general, suitable vectors can either be chosen from those that are commercially available or they can be constructed using standard recombinant DNA techniques known in the art. (See, e.g., Molecular Cloning: A Laboratory Manual: 2nd edition, Sambrook et al., 1989, Cold Spring Harbor Laboratory Press.) The vector comprises DNA that encodes for the chimeric RdCVF protein construct. The chimeric RdCVF protein may or may not contain the initiating methionine of the RdCVF protein. A gene delivery vehicle is any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, viruses, such as baculovirus, adeno-associated virus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

Gene delivery, gene transfer, and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

The exogenous polynucleotide is inserted into a vector such as adenovirus, adeno-associated virus (AAV), retrovirus, lentivirus, naked plasmid, plasmid/liposome complex, etc. for delivery to the host via intravenous, intramuscular, intraportal or other route of administration. Expression vectors which can be used in the methods and compositions of the present invention include, for example, viral vectors. One of the most frequently used methods of administration of gene therapy, both in vivo and ex vivo, is the use of viral vectors for delivery of the gene. Many species of virus are known, and many have been studied for gene therapy purposes. The most commonly used viral vectors include those derived from adenoviruses, adeno-associated viruses (AAV) and retroviruses, including lentiviruses, such as human immunodeficiency virus (HIV). In aspects where the vector is a DNA viral vector, such as an adenovirus (Ad) or adeno-associated virus (AAV), a vector construct refers to the polynucleotide comprising the viral genome or part thereof, and a transgene comprising DNA encoding for the chimeric RdCVF protein construct of the instant invention. Adenoviruses (Ads) are a relatively well characterized, homogenous group of viruses, including over 50 serotypes. See, e.g., International PCT Application No. WO 95/27071. Ads are easy to grow and do not require integration into the host cell genome. Recombinant Ad derived vectors, particularly those that reduce the potential for recombination and generation of wild-type virus, have also been constructed. See, International PCT Application Nos. WO 95/00655 and WO 95/11984.

Adenovirus is a non-enveloped, nuclear DNA virus with a genome of about 36 kb, which has been well-characterized through studies in classical genetics and molecular biology (Hurwitz, M. S., Adenoviruses *Virology*, 3$^{rd}$ edition, Fields et al., eds., Raven Press, New York, 1996; Hitt, M. M. et al., Adenovirus Vectors, *The Development of Human Gene Therapy*, Friedman, T. ed., Cold Spring Harbor Laboratory Press, New York 1999). The viral genes are classified into early (designated E1-E4) and late (designated L1-L5) transcriptional units, referring to the generation of two temporal classes of viral proteins. The demarcation of these events is viral DNA replication. The human adenoviruses are divided into numerous serotypes (approximately 47, numbered accordingly and classified into 6 groups: A, B, C, D, E and F), based upon properties including hemaglutination of red blood cells, oncogenicity, DNA and protein amino acid compositions and homologies, and antigenic relationships.

Recombinant adenoviral vectors have several advantages for use as gene delivery vehicles, including tropism for both dividing and non-dividing cells, minimal pathogenic potential, ability to replicate to high titer for preparation of vector stocks, and the potential to carry large inserts (Berkner, K. L., *Curr. Top. Micro. Immunol.* 158:39-66, 1992; Jolly, D., *Cancer Gene Therapy* 1:51-64 1994). Adenoviral vectors with deletions of various adenoviral gene sequences, such as pseudoadenoviral vectors (PAVs) and partially-deleted adenoviral (termed "DeAd"), have been designed to take advantage of the desirable features of adenovirus which render it a suitable vehicle for delivery of nucleic acids to recipient cells.

AAV vectors are derived from single-stranded (ss) DNA parvoviruses that are nonpathogenic for mammals (reviewed in Muzyscka (1992) Curr. Top. Microb. Immunol., 158:97-129). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit.

In the methods of the invention, AAV of any serotype can be used. The serotype of the viral vector used in certain embodiments of the invention is selected from the group consisting from AAV1, AAV2, AAV3, AAV4, AAV5, AAV6, AAV7, and AAV8 (see, e.g., Gao et al. (2002) PNAS, 99:11854-11859; and Viral Vectors for Gene Therapy: Methods and Protocols, ed. Machida, Humana Press, 2003). Other serotype besides those listed herein can be used. Furthermore, pseudotyped AAV vectors may also be utilized in the methods described herein. Pseudotyped AAV vectors are those which contain the genome of one AAV serotype in the capsid of a second AAV serotype; for example, an AAV vector that contains the AAV2 capsid and the AAV1 genome or an AAV vector that contains the AAV5 capsid and the AAV 2 genome (Auricchio et al., (2001) Hum. Mol. Genet., 10(26):3075-81).

In an illustrative embodiment, AAV is AAV2 or AAV1. Adeno-associated virus of many serotypes, especially AAV2, have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003). The terms "genome particles (gp)," or "genome equivalents," or "genome copies" (gc) as used in reference to a viral titer, refer to the number of virions containing the recombinant AAV DNA genome, regardless of infectivity or functionality. The number of genome particles in a particular vector preparation can be measured by procedures such as described in the Examples herein, or for example, in Clark et al. (1999) Hum. Gene Ther., 10:1031-1039; Veldwijk et al. (2002) Mol. Ther., 6:272-278. The terms "infection unit (iu)," "infectious particle," or "replication unit," as used in reference to a viral titer, refer to the number of infectious and replication-competent recombinant AAV vector particles as measured by the infectious center assay, also known as replication center assay, as described, for example, in McLaughlin et al. (1988) J. Virol., 62:1963-1973. The term "transducing unit (tu)" as used in reference to a viral titer, refers to the number of infectious recombinant AAV vector particles that result in the production of a functional transgene product as measured in functional assays such as described in Examples herein, or for example, in Xiao et al. (1997) Exp. Neurobiol., 144:113-124; or in Fisher et al. (1996) J. Virol., 70:520-532 (LFU assay). The term "dnase resistant particles (drp)" as used in reference to a viral titer, refers to the number of recombinant AAV vector particles that are resistant to DNase treatment. It is typically measured using DNA dot-blot hybridization as known in the art.

Retrovirus vectors are a common tool for gene delivery (Miller, *Nature* (1992) 357:455-460). The ability of retrovirus vectors to deliver an unrearranged, single copy gene into a broad range of rodent, primate and human somatic cells makes retroviral vectors well suited for transferring genes to a cell. Retroviruses are RNA viruses wherein the viral genome is RNA. When a host cell is infected with a retrovirus, the genomic RNA is reverse transcribed into a DNA intermediate which is integrated very efficiently into the chromosomal DNA of infected cells. This integrated DNA intermediate is referred to as a provirus. Transcription of the provirus and assembly into infectious virus occurs in the presence of an appropriate helper virus or in a cell line containing appropriate sequences enabling encapsidation without coincident production of a contaminating helper virus. A helper virus is not required for the production of the recombinant retrovirus if the sequences for encapsidation are provided by co-transfection with appropriate vectors.

The retroviral genome and the proviral DNA have three genes: the gag, the pol, and the env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication. Lentiviruses have additional genes including vit vpr, tat, rev, vpu, nef, and vpx (in HIV-1, HIV-2 and/or SIV). Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all varion proteins.

Lentiviruses are complex retroviruses which, in addition to the common retroviral genes gag, pol and env, contain other genes with regulatory or structural function. The higher complexity enables the lentivirus to modulate the life cycle thereof, as in the course of latent infection. A typical lentivirus is the human immunodeficiency virus (HIV), the etiologic agent of AIDS. In vivo, HIV can infect terminally differentiated cells that rarely divide, such as lymphocytes and macrophages. In vitro, HIV can infect primary cultures of monocyte-derived macrophages (MDM) as well as HeLa-Cd4 or T lymphoid cells arrested in the cell cycle by treatment with aphidicolin or gamma irradiation. Infection of cells is dependent on the active nuclear import of HIV preintegration complexes through the nuclear pores of the target cells. That occurs by the interaction of multiple, partly redundant, molecular determinants in the complex with the nuclear import machinery of the target cell. Identified determinants include a functional nuclear localization signal (NLS) in the gag matrix (MA) protein, the karyophilic virion-associated protein, vpr, and a C-terminal phosphotyrosine residue in the gag MA protein. The use of retroviruses for gene therapy is described, for example, in U.S. Pat. No. 6,013,516; and U.S. Pat. No. 5,994,136, the disclosures of which are hereby incorporated herein by reference.

Other methods for delivery of DNA to cells do not use viruses for delivery. For example, cationic amphiphilic compounds can be used to deliver the nucleic acid of the present invention. Because compounds designed to facilitate intracellular delivery of biologically active molecules must interact with both non-polar and polar environments (in or on, for example, the plasma membrane, tissue fluids, compartments within the cell, and the biologically active molecular itself), such compounds are designed typically to contain both polar and non-polar domains. Compounds having both such domains may be termed amphiphiles, and many lipids and synthetic lipids that have been disclosed for use in facilitating such intracellular delivery (whether for in vitro or in vivo application) meet this definition. One particularly important class of such amphiphiles is the cationic amphiphiles. In general, cationic amphiphiles have polar groups that are capable of being positively charged at or around physiological pH, and this property is understood in the art to be important in defining how the amphiphiles interact with the many types of biologically active (therapeutic) molecules including, for example, negatively charged polynucleotides such as DNA.

The use of compositions comprising cationic amphiphilic compounds for gene delivery is described, for example, in U.S. Pat. No. 5,049,386; U.S. Pat. No. 5,279,833; U.S. Pat. No. 5,650,096; U.S. Pat. No. 5,747,471; U.S. Pat. No. 5,767,099; U.S. Pat. No. 5,910,487; U.S. Pat. No. 5,719,131; U.S. Pat. No. 5,840,710; U.S. Pat. No. 5,783,565; U.S. Pat. No. 5,925,628; U.S. Pat. No. 5,912,239; U.S. Pat. No. 5,942,634; U.S. Pat. No. 5,948,925; U.S. Pat. No. 6,022,874; U.S. Pat. No. 5,994,317; U.S. Pat. No. 5,861,397; U.S. Pat. No. 5,952,916; U.S. Pat. No. 5,948,767; U.S. Pat. No. 5,939,401; and U.S. Pat. No. 5,935,936, the disclosures of which are hereby incorporated herein by reference.

In addition, nucleic acid of the present invention can be delivered using "naked DNA." Methods for delivering a non-infectious, non-integrating DNA sequence encoding a desired polypeptide or peptide operably linked to a promoter, free from association with transfection-facilitating proteins, viral particles, liposomal formulations, charged lipids and calcium phosphate precipitating agents are described in U.S. Pat. No. 5,580,859; U.S. Pat. No. 5,963, 622; U.S. Pat. No. 5,910,488; the disclosures of which are hereby incorporated herein by reference.

Gene transfer systems that combine viral and nonviral components have also been reported. Cristiano et al., (1993) *Proc. Natl. Acad. Sci. USA* 90:11548; Wu et al. (1994) *J. Biol. Chem.* 269:11542; Wagner et al. (1992) *Proc. Natl. Acad. Sci. USA* 89:6099; Yoshimura et al. (1993) *J. Biol. Chem.* 268:2300; Curiel et al. (1991) *Proc. Natl. Acad. Sci. USA* 88:8850; Kupfer et al. (1994) *Human Gene Ther.* 5:1437; and Gottschalk et al. (1994) *Gene Ther.* 1:185. In most cases, adenovirus has been incorporated into the gene delivery systems to take advantage of its endosomolytic properties. The reported combinations of viral and nonviral components generally involve either covalent attachment of the adenovirus to a gene delivery complex or co-internalization of unbound adenovirus with cationic lipid: DNA complexes.

Signal peptides, as used herein, are peptide chains that direct post-translational transport of a protein. Signal peptides may also be referred to as targeting signals, signal sequences, transit peptides or localizing signals. Signal peptides are involved in directing proteins to particular organelles such as the nucleus, mitochondrial matrix, endoplasmic reticulum, chloroplast, apoplast and peroxixome.

Figure 17:
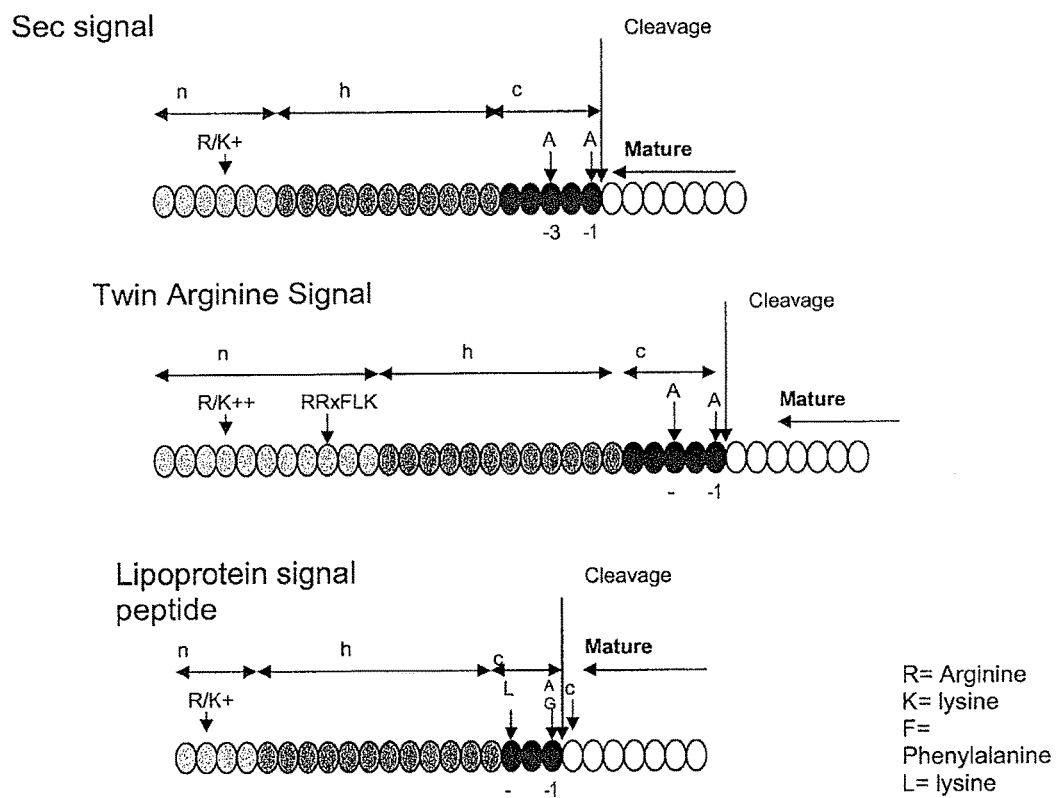
FIG. 17 shows example signal peptides according to some embodiments.

The structure of a typical Signal peptide includes three distinct regions: (i) an N-terminal region (n-region) that contains a number of positively charged amino acids (lysines and arginines); (ii) a central hydrophobic core region (h-region); (iii) a hydrophilic cleavage region (c-region) that contains the sequence motif recognized by the signal peptidase. (von Heijne, G. (1983) Eur. J. Biochem., 133, 17-21; von Heijne, G. (1985) J. Mol. Biol., 184, 99-105; von Heijne, G. (1997) Protein Engineering (10), pp 1-6). The (−3, −1) rule states that residues at −3 and −1 must be small and neutral for cleavage to occur efficiently (von Heijne, 1997). FIG. 17 demonstrate the structures of various of types of signal peptides. Common examples of proteins with signal peptides include BMP7, BMP2, CNTF, BDNF, GDNF, HGF, VEGF, LIF.

Some signal peptides are cleaved from the protein by signal peptidase after the proteins are'transported. Non-limiting examples of signal peptides include those present in secreted proteins bovine growth hormone, bovine proalbumin, human proinsulin, human interferon-γ, human α-fibrinogen, human IgG heavy chain, rat amylase, murine α-fetoprotein, chicken lysozyme, Zea mays rein protein 22.1. In some embodiments, preferred non-limiting examples of signal peptides include those present in secreted proteins human growth hormone (HGH), brain derived neurotrophic factor (BDNF), insulin growth factor 1 (IGF1), and β-glucoronidase (GUSB).

In some embodiments of the invention, the signal peptide nucleotide sequence exists at or near the N terminal or the C terminal of a protein. In preferred embodiments, the signal peptide exists at or near the N terminal of the protein. In preferred embodiments, the signal peptide directs transit of the protein to secretory pathways and, in particular, to the endoplasmic reticulum (ER). In some embodiments, the signal peptide associates or binds to ER bound receptors, or signal recognition particles in the cytosol. In some embodiments, the signal peptide facilitates protein transport from the cytoplasm to destinations outside the cell. In some embodiments, the signal peptide sequence is selected from a signal peptide sequence from efficiently secreted proteins. Signal peptide sequences may be selected from naturally occurring, signal peptide sequences, derivatives thereof, or a synthetic designed sequence. In some embodiments, non-limiting parameters for a designed signal peptide sequences include a sequence of preferably 3-40 residues, comprising a 3- to 20-residue hydrophobic core flanked by several relatively hydrophilic residues.

In some embodiments, the signal peptide sequence lacks a hydrophobic core. Non-limiting examples of mammalian secretory proteins that lack a typical hydrophobic signal sequence include human IL-1α, IL1β, bFGF, aFGF, PDEGF, anticoagulant protein, lectin L-14, ATL-derived factor, Factor XIIIa, Anchorin CII, lipocortin I, parathymosin, α-prothymosin, and rodent transglutaminase, parathymosin and MDGI.

In some embodiments, the signal peptide-encoding nucleotide sequence encodes a signal peptide disclosed herein.

Furin catalyses a biochemical reaction, the proteolytic maturation of proprotein substrates in the secretory pathway. Furin is subtilisin-like serine endoprotease and known as a proprotein convertase. It is expressed in cells and tissues, mainly localized in the trans-Golgi network. A typical consensus site that furin cleaves is positioned after the carboxy-terminal arginine (Arg) residue in the sequence -Arg-Xaa-(Lys/Arg)-Arg↓- (where Lys is lysine, Xaa is any amino acid and ↓ identifies the cleavage site) (SEQ ID NO:3). In some embodiments, the nucleotide sequence encoding for the furin cleavage marker is a sequence encoding the amino acid sequence of -Xaa-Arg-Xaa-(Lys/Arg)-Arg↓- (where Xaa is any amino acid and ↓ identifies the cleavage site) (SEQ ID NO:4). In some embodiments, the nucleotide sequence encoding for the furin cleavage marker is a sequence encoding the amino acid sequence of -Arg-Xaa-(Lys/Arg)-Arg↓- (where X is any amino acid and ↓ identifies the cleavage site) (SEQ ID NO:3). In some preferred embodiments, the nucleotide sequence encoding for the furin cleavage marker is a sequence encoding the amino acid sequence of KRIKR (SEQ ID NO:2).

In some embodiments, the expression vector optionally comprises a sequence encoding for an amino acid linker. In some embodiments the expression vector encodes for an amino acid linker wherein the amino acid linker separates the signal peptide sequence from the furin cleavage marker. In some preferred embodiments, the signal peptide-encoding sequence and the sequence encoding the furin cleavage marker are separated by a sequence encoding an amino acid linker. In some embodiments the expression vector may encode an amino acid linker comprised of 2-50 amino acids. In some embodiments the amino acid linker is comprised of 10-25 acids. In preferred embodiments the amino acid linker is comprised of 15-20 amino acids. In even more preferred embodiments, the amino acid linker is comprised of the sequence MPLESGLSSEDSASSESFA (SEQ ID NO:1), although variations of the length and amino acid choice may also be included.

In some embodiments, the expression vector disclosed herein, contains, in addition, a nucleotide sequence encoding an amino acid tag that enables the purification of the RdCVF protein using affinity chromatography. In some embodiments, the location of the nucleotide sequence encoding the amino acid tag is located at the C terminus. For example, the amino acid tag is EDQVDPRLIDGK (SEQ ID NO:5), a sequence from protein C that encodes the epitope for a monoclonal antibody HPC4. Inclusion of this peptide epitope enables the purification of the RdCVF protein using HPC4 affinity chromatography.

"Promoter" refers to a regulatory element that directs the transcription of a nucleic acid to which it is operably linked. A promoter used to control the transcription of the recombinant proteins herein may be chosen from any of those which are functional in the host cell. Non-limiting examples of promoters include SV40 early promoter, adenovirus major late promoter, herpes simplex (HSV) thymidine kinase promoter, rous sarcoma (RSV) LTR promoter, human cytomegalovirus (CMV) immediate early promoter, mouse mammary tumor virus (MMTV) LTR promoter, interferon-β promoter, heat shock protein 70 (hsp 70) promoter, as well as many others well known in the art. In preferred embodiments, the promoter is SV40 early promoter or the 3 kb hamster β-actin promoter.

"Host cells" as used herein, refers to a cell that contains heterologous DNA that has been introduced into the cell by any means. Non-limiting examples of means for introduction of DNA into the cell include electroporation, calcium phosphate precipitation, microinjection, transformation, viral infection, DEAE-Dextran transfection, liposome-mediated transfection, transduction using viral vectors and the like.

The invention further provides host cells that have been transfected with a vector of the invention disclosed herein. Such a host cell can be a prokaryotic cell or a eukaryotic cell. Host cells can either be cells in culture or be present in an animal.

Non-limiting example of non-mammalian cell line includes insect and *Drosophila* cells. Non-limiting examples of mammalian cell lines include 3T3 cells, COS cells, human osteosarcoma cells, MRC-5 cells, BHK cells, VERO cells, CHO cells, rCHO-tPA cells, rCHO-Hep B Surface Antigen cells, HEK 293 cells, rHEK 293 cells, rC127-Hep B Surface Antigen cells, Normal Human fibroblast cells, Stroma cells, Hepatocyte cells, PER.C6 cells and human permanent amniocytic cells. Examples of host cells in culture include, but are not limited to, HeLa cells, CHO cells, NSO, HEK cells, BHK cells, NIH-3T3, MDCK cells, and COS cells. Host cells in culture can be grown either in suspension or on microcarriers. In some embodiments, host cells are chosen from cells that are capable of secreting the RdCVF protein, or derivative thereof, into the surrounding medium, so that the expressed protein according to the invention can be directly purified from the media. In a preferred embodiment, the host cells are mammalian cells COS or CHO cells.

Many suitable expression systems can be employed for the production of proteins using vectors of the invention. The expression of the protein may be stable or transient expression. The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. Transient expression comprises introduction of the DNA encoding for the chimeric RdCVF protein into the cell wherein the DNA does not contains an origin of replication compatible with the host cell or does not integrate into a replicon or chromosome of the host cell but rather is maintained episomally. One particular expression system employs a dihydrofolate reductase (DHFR) gene which is introduced into a vector of the invention or a variant thereof. Alternatively, an expression vector expressing DHFR can be co-transfected into the host cell, if a DHFR-deficient cell is used for expression. When increasing concentrations of methotrexate (MTX), a competitive inhibitor of the essential enzyme DHFR, are applied to the transfected cells, only cells with higher expression levels of DHFR survive. As MTX levels are increased further, only cells which amplify the copy number of the DHFR gene survive. In this way, by increasing the copy number of the vector, increased expression of the heterologous nucleic acid can be achieved, thereby leading to increased protein production. A second expression system employs a glutamin synthetase (GS) gene that is introduced into a vector of the invention or a variant thereof. Addition of a competitive inhibitor of GS, e.g., methionine sulphoximine (MSX), is used for increasing the copy number of the vector leading to increased protein production. Any suitable prokaryotic or eukaryotic expression system can be used for expression of proteins using vectors of the invention.

"Secretion" as used herein means exportation of product through the plasma membrane and into the medium supporting the cell culture. In some embodiments, preferred products of this invention are any proteins expressed by the vectors disclosed herein. In some preferred embodiments, non-limiting examples of products are rod-derived cone viability factor (RdCVF) or derivatives thereof.

The protein of the present invention can be produced by cultivating transformants, especially mammalian cells, as mentioned above and allowing them to secrete the protein into the culture supernatant.

A culture filtrate (supernatant) may be obtained by a method such as filtration or centrifugation of the obtained culture, and the protein of the present invention is purified and isolated from the culture filtrate by methods commonly used in order to purify and isolate a natural or synthetic protein. Non-limiting examples of the isolation and purification method are a method utilizing solubility, such as salting out and solvent precipitation method; a method utilizing the difference in molecular weight, such as dialysis, ultrafiltration, gel filtration, and sodium dodecyl sulfate-polyacrylamide gel electrophoresis; a method utilizing charge, such as ion exchange chromatography and hydroxylapatite chromatography; a method utilizing specific affinity, such as affinity column chromatography; a method utilizing the difference in hydrophobicity, such as reverse phase high performance liquid chromatography; and a method utilizing the difference in isoelectric point, such as isoelectric focusing. An example of RdCVF purification using HPC4 affinity chromatography is described in Example 4.

Ocular diseases that may be treated according to the present invention include, but are not limited to, Stargardt's disease, Retinitis Pigmentosa, Age-related Macular Degeneration (AMD, Dry & Wet forms), Glaucoma/Ocular Hypertension, Diabetic Retinopathy, Thyroid related eye disease—Grave's disease, Diseases associated with Retinal Pigmented Epithelial Cells, Anterior segment disease, Lens disease/Cataracts, Eye cup disorders, Uveitis.

For delivery of the RdCVF protein of the instant invention to the eye (whether via gene therapy or protein therapy), administration will typically be local. This has the advantage of limiting the amount of material (protein or DNA) that needs to be administered and limiting systemic side-effects. Many possible modes of delivery can be used, including, but not limited to: topical administration on the cornea by a gene gun; subconjunctival injection, intracameral injection, via eye drops to the cornea, injection into the anterior chamber via the termporal limbus, intrastromal injection, corneal application combined with electrical pulses, intracorneal injection, subretinal injection, intravitreal injection (e.g., front, mid or back vitreal injection), and intraocular injection. Alternatively cells can be transfected or transduced ex vivo and delivered by intraocular implantation. See, Auricchio, *Mol. Ther.* 6: 490-494, 2002; Bennett, *Nature Med.* 2: 649-654, 1996; Borrás, *Experimental Eye Research* 76: 643-652, 2003; Chaum, *Survey of Ophthalmology* 47: 449-469, 2002; Campochiaro, *Expert Opinions in Biological Therapy* 2: 537-544 (2002); Lai, *Gene Therapy* 9: 804 813, 2002; Pleyer, *Progress in Retinal and Eye Research*, 22: 277-293, 2003.

The effects of various proposed therapeutic agents and administrations can be tested in suitable animal models for particular diseases. For example, the effect of delivering RdCVF to the retina can be tested in a mouse model of retinitis pigmentosa (rd1).

For the prevention or treatment of disease, the appropriate dosage of the RdCVF protein of the present invention (protein or gene therapy) will depend on the type of disease to be treated, the severity and course of the disease, whether the RdCVF is administered for preventive or therapeutic purposes, previous therapy, the patient's clinical history and response to the RdCVF, and the discretion of the attending physician. The RdCVF is suitably administered to the patient at one time or over a series of treatments. In a combination therapy regimen, the compositions of the present invention are administered in a therapeutically effective or synergistic amount. As used herein, a therapeutically effective amount is such that co-administration of RdCVF and one or more other therapeutic agents, or administration of a composition of the present invention, results in reduction or inhibition of the targeting disease or condition. A therapeutically synergistic amount is that amount of RdCVF and one or more other therapeutic agents necessary to synergistically or significantly reduce or eliminate conditions or symptoms associated with a particular disease.

Depending on the type and severity of the disease, the RdCVF of the instant invention may be administered so that the local concentration provided is about 100 pg/ml to about 100 µg/ml, 1 ng/ml to about 95 µg/ml, 10 ng/ml to about 85 µg/ml, 100 ng/ml to about 75 µg/ml, from about 100 ng/ml to about 50 µg/ml, from about 1 µg/ml to about 25 µg/ml, from about 1 µg/ml to about 15 µg/ml, from about 1 µg/ml to about 10 µg/ml, or from about 1 µg/ml to about 4 µg/ml. When the RdCVF is delivered by gene therapy through viral virions, the dose may be from about $2\times10^6$ to about $2\times10^{12}$, from about $2\times10^7$ to about $2\times10^{11}$ drp, or from about $2\times10^8$ to about $2\times10^{10}$ drp per unit dose. When the RdCVF is administered by protein therapy, the dose may be from about 0.1 mg to about 50 mg, from about 0.1 mg to about 25 mg, from about 0.1 mg to about 10 mg, from about 0.5 mg to about 5 mg, or from about 0.5 mg to about 2.5 mg per unit dose.

The RdCVF of the present invention may be administered as a single dose or repeatedly whether as the protein or as a gene therapy vector). For repeated administrations over several days or longer, depending on the condition, the treatment is sustained until a desired suppression of disease symptoms occurs. The progress of the therapy of the invention is monitored by conventional techniques and assays.

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Diego, Calif. (1990); Freshney, R. I., *Culture of Animal Cells: A Manual of Basic Technique*, 2nd Ed., Alan Liss, Inc. New York, N.Y. (1987); Murray, E. J., ed., *Gene Transfer and Expression Protocols*, pp. 109-128, The Humana Press Inc., Clifton, N.J. and Lewin, B., *Genes VI*, Oxford University Press, New York (1997). All methods and techniques described herein are known to those skilled in the art.

The following examples are offered to illustrate but not to limit the invention. All references disclosed herein are expressly incorporated by reference.

Example 1

Generation of cDNAs Encoding RdCVF with Different Signal Peptides

Expression vectors were constructed to evaluate the efficiency of RdCVF expression using a number of signal peptides. Signal peptides from brain derived neurotrophic factor (BDNF), insulin growth factor 1 (IGF1), and beta-glucoronidase signal peptide (GUSB) were evaluated.

In the case of these signal peptides, the relevant sequences were cloned immediately before the initiating methionine for RdCVF. In FIGS. 5-10, the signal peptide sequence (depicted in bold in the following sequences) is followed by an amino acid linker sequence (depicted by underline) followed by a furin cleavage site depicted in italics. The remainder of the sequence indicates the amino acid sequence for RdCVF (Short Form or Long Form). The different signal peptides are cleaved by their respective signal peptidases in the ER (specific site depicted by arrow). Inclusion of the furin cleavage site KRIKR, results in removal of the remaining amino acids before the initiating methionine for RdCVF. Furin is an enzyme that resides in the Golgi, and cleaves directly after the terminal Arginine in the KRIKR sequence. The Furin cleavage site is depicted by arrow.

Example 2

Human Growth Hormone Signal Peptide LONG FORM Human RdCVF

Expression vectors were constructed to evaluate the efficiency of RdCVF expression using the signal peptide from HGH signal peptide (Human growth hormone signal peptide). For the HGH signal peptide, the cDNA construct is designed such that the initiating methionine for RdCVF is removed resulting in a RdCVF protein that initiates with an Alanine.

In FIGS. 11 and 12, the signal peptide sequence is depicted in bold in the following sequences. The remainder of the sequence indicates the amino acid sequence for RdCVF (Short Form or Long Form). The signal peptide is cleaved by the respective signal peptidase in the ER (specific site depicted by arrow).

Example 3

Human Growth Hormone Signal Peptide LONG FORM Human RdCVF HPC4 Tag

As in Example 2, expression vectors were constructed to evaluate the efficiency of RdCVF expression using the signal peptide from HGH signal peptide (Human growth hormone signal peptide) that contain a purification tag. For the HGH signal peptide, the cDNA construct is designed such that the initiating methionine for RdCVF is removed resulting in a RdCVF protein that initiates with an Alanine. In FIGS. 13 and 14, the signal peptide sequence is depicted in bold. The remainder of the sequence indicates the amino acid sequence for RdCVF (Short Form or Long Form). The signal peptide is cleaved by the respective signal peptidase in the ER (specific site depicted by arrow). The twelve amino acid HPC4 tag is depicted by underline.

Example 4

Method to Produce Purified RdCVF Protein (LF) and (SF) from Mammalian Cells

| Vector | Insert | Length | Signal sequence | Cell line |
|--------|--------|--------|-----------------|-----------|
| pGZ6 | rhRdCVF | short form | hGH | CHODXB11 |
| pGZ6 | rhRdCVF | long form | hGH | CHODXB11 |

CHO DXB11 Transient Expression

PGZ6 vectors expressing RdCVF(LF) and RdCVF(SF) were generated. The signal peptide from human growth hormone was included at the N terminus of RdCVF sequence to increase secretion of the protein. In addition the epitope for antibody HPC4 was included at the C terminus. The twelve amino acid tag (EDQVDPRLIDGK (SEQ ID NO:5)), is a sequence from protein C and encodes the epitope for a monoclonal antibody HPC4. Inclusion of this peptide epitope enables the purification of the RdCVF protein using HPC4 affinity chromatography in the presence of calcium ions. Release of bound RdCVF from the HPC4 affinity resin is achieved by elution with EGTA containing buffers. Transient transfection in CHO DXB11 cells confirmed expression of RdCVF-HGH in the mammalian expression system. Transfections were done in duplicate with a change of media after 4 hour incubation to either DMEM+1% FBS or ExCell 302. Samples were harvested after 72 h and examined by HPC4 western. All transient transfections showed expression of the recombinant proteins in the conditioned medium.

Example 5

Method to Produce Purified RdCVF Protein (LF) and (SF) from Mammalian Cells

CHO DXB11 Stable Expression

Figure 4:
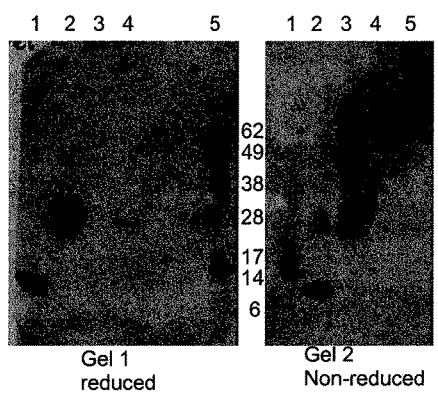
FIG. 4 shows expressed protein samples of pGZ6 RdCVF SF and pGZ6 RdCVF LF by HPC4 Western analysis according to one embodiment.

Expression was observed in the transient transfection with CHODXB11 mammalian system and stable cell line developments were initiated. An expression system utilizing dihydrofolate reductase (DHFR) selection and methotrexate (MTX) amplification was used. The vector pGZ6 was derived from the pCLHAXSV2DHFR plasmid, so as to contain the 3 kb hamster β-actin promoter in addition to a DHFR gene under the control of the SV40 early promoter. The pCLHAXSV2DHFR plasmid has been previously described by Cole et al. (1993) Biotechnology, 11:1014-1024. Briefly, the metallothionine (MT) promoter in the pCLHAXSV2DHFR vector was replaced with the β-actin promoter to create the pGZ6 vector. The DHFR-deficient CHO-K1 cell line DXB11 was transfected in triplicate with the RdCVF expression vectors. Typically, for industrial production of proteins, high expression is achieved by selecting cells with a higher gene copy number through a process that involves increasing the concentration of MTX. The RdCVF pools initially selected at 100 nM MTX were amplified by selection at five-fold higher levels of MTX (100 nM). Cells stably expressing RdCVF were selected by growth in 100 nM MTX. Cells recovered from the 100 nM MTX selection were cryopreserved and a small scale expression experiment was performed. A T150 cell culture flask of each of the four stables above was seeded. Cells were confluent 2 days later and medium was changed from FBS containing medium to Serum-free Excel 302. Samples were removed after 72 hrs and analyzed by HPC4 Western analysis, see FIG. 4. pGZ6 (hGH) RdCVF SF and pGZ6 (hGH) RdCVF LF expressed protein at the appropriate size in reduced SDS PAGE gels HPC4 Western analysis. Selection of single clones of CHO-DXB11 expressing hRdCVF long and short forms (with growth hormone signal sequence) was achieved by limiting dilution. Single clones were isolated and used for purification studies.

Example 6

Reductase Activity of RdCVF(LF)

Figure 3:
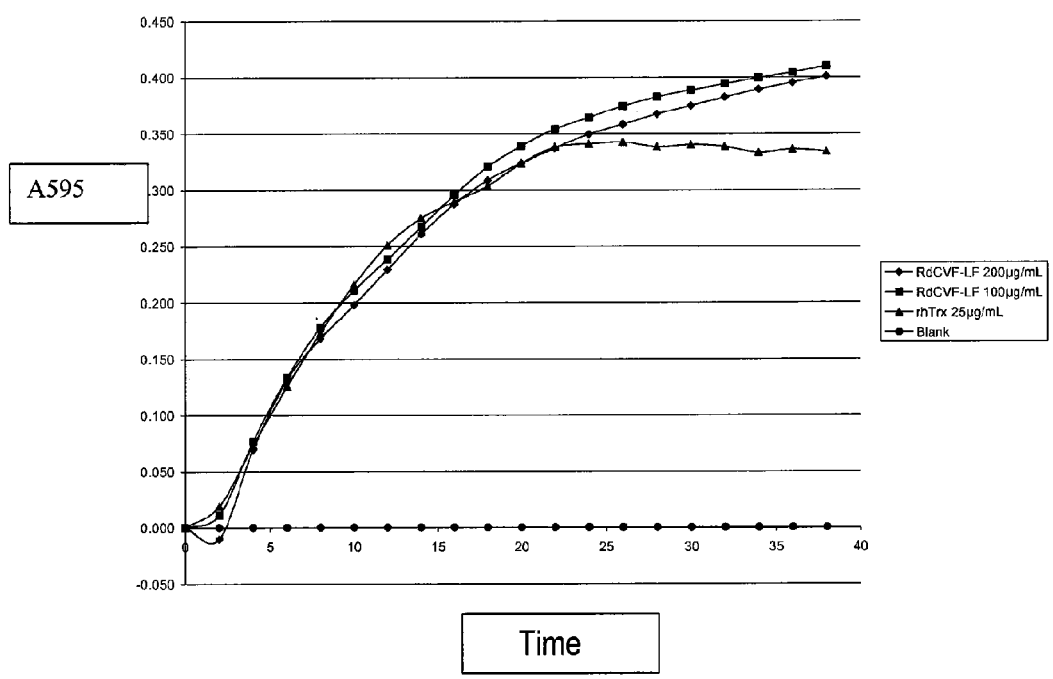
FIG. 3 shows absorbance measurements at 595 nm as a function of time indicating oxidoreductase activity of RdCVF according to one embodiment. In this assay, insulin polypeptide chains that are normally held together by a disulfide bond are reduced in the presence of either RdCVF (LF) or Thioredoxin protein. Reduced insulin forms a precipitate which is measured as an increase in absorbance at 595 nm RdCVF(LF) has measurable oxidoreductase activity as shown here.

The insulin disulfide reductase activity of purified RdCVF (LF) protein was measured by monitoring the increase in the turbidity of reaction mixtures due to the formation of fine precipitates of the dissociated B chain of insulin (FIG. 3). In a negative control with dithiothreitol alone, no precipitation was observed during incubation for up to 40 minutes. The addition of RdCVF (LF) or Trx1 resulted in an increase in optical density at A595 nm.

Example 7

TUNEL Assay

Figure 18:
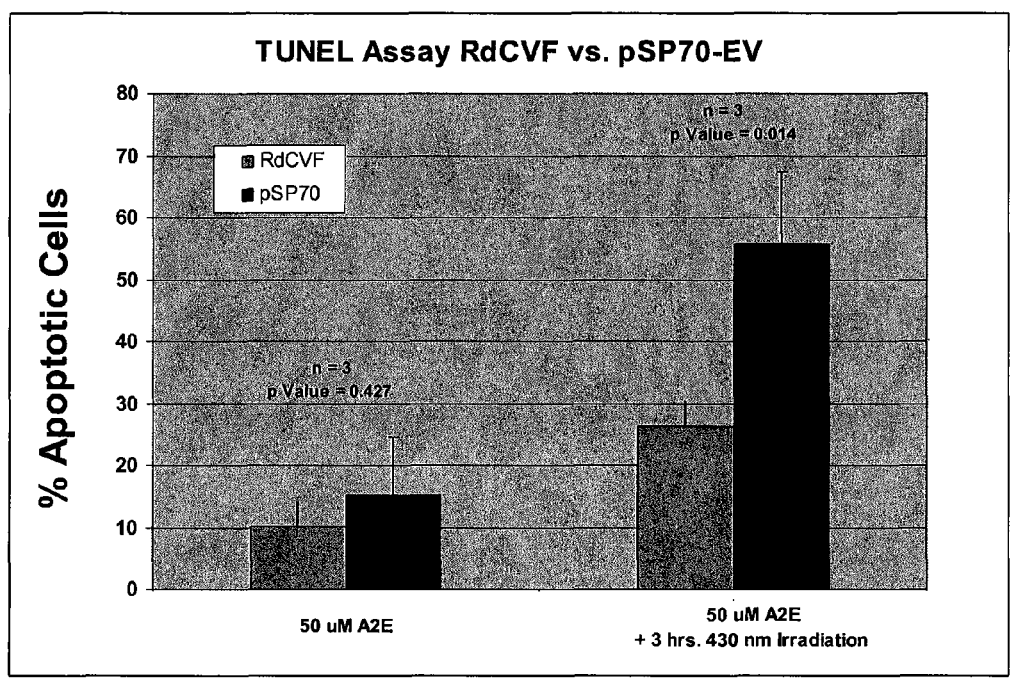
FIG. 18 shows a TUNEL assay result according to one embodiment.

A2E is a bis retinoid pyridinium that accumulates as a lipofuscin pigment in RPE cells in association with aging and in some inherited forms of retinal degeneration eg dry AMD and Stargardt;s disease. Upon photooxidation the A2E forms oxiranes (these are toxic). RdCVF(LF) protein protects A2E/Blue light irradiated cells from photooxidation and decreases apoptosis. The number of apoptotic cells is reduced by ~30% compared to control cells, following treatment with RdCVF(LF) protein (FIG. 19). FIG. 18 is the average of 3 separate experiments of RdCVF (LF) treated cells compared to control pSP70-Ev empty vector.

Example 8

In Vivo Evaluation of RdCVF (LF)

Secretable forms of RdCVF(LF) are evaluated in a model of retinal degeneration, the rd10 mouse. In this model there is a missense mutation in the rod phosphodiesterase which results in rod degeneration that starts at P18. Later, cones are also lost. AAV2/5 RdCVF (LF) are delivered to P0 rd10 pups by sub retinal injection (1e 9 DRPs, 1 ul); control eyes are injected with titer matched AAV2/8 EV. Mice are sacrificed at various times post injection, P18, P25, P32 & P46. At each time point retinal thickness is measured following retinal sectioning, in an additional cohort cone survival is assessed by PNA lectin labeling of cones followed by cone counting using morphometric analysis. Rd10 mice treated with AAV2/5 RdCVF(LF) demonstrates a greater number of surviving cones resulting in a thicker outer nuclear layer (ONL) following RdCVF(LF) treatment.

The invention claimed is:

1. An expression vector for expression of rod-derived cone viability factor (RdCVF) comprising
   a) a RdCVF-encoding nucleotide sequence;
   b) a signal peptide-encoding nucleotide sequence positioned upstream of the RdCVF-encoding nucleotide sequence, wherein the signal peptide-encoding sequence encodes the signal peptide of insulin growth factor-1 (IGF-1) and directs secretion of expressed RdCVF; and
   c) a nucleotide sequence encoding a furin cleavage marker located downstream of the signal peptide-encoding nucleotide sequence and upstream of the RdCVF-encoding nucleotide sequence, wherein the signal peptide-encoding sequence and the furin cleavage marker sequence are separated by a nucleotide sequence encoding SEQ ID NO: 1.

2. The expression vector of claim 1, wherein the RdCVF-encoding nucleotide sequence lacks the initiating methionine coding sequence.

3. The expression vector of claim 1, wherein the RdCVF-encoding sequence encodes the long form of RdCVF (SEQ ID NO:26).

4. The expression vector of claim 1, wherein the signal peptide is the IGF-1 signal peptide (SEQ ID NO:30).

5. The expression vector of claim 1, wherein the nucleotide sequence encoding the furin cleavage marker encodes the amino acid sequence KRIKR (SEQ ID NO:3).

6. The expression vector of claim 1, wherein said vector comprises a nucleic acid sequence that codes for the amino acid sequence of SEQ ID NO:10.

7. The expression vector of claim 1, wherein said vector comprises SEQ ID NO:11.

8. An expression vector for expression of rod-derived cone viability factor (RdCVF) comprising
  a) a RdCVF-encoding nucleotide sequence lacking the initiating methionine coding sequence; and
  b) an exogenous signal peptide-encoding nucleotide sequence positioned upstream of the RdCVF-encoding nucleotide sequence, wherein the exogenous signal peptide-encoding sequence is the signal peptide of insulin growth factor-1 (IGF-1) and directs secretion of expressed RdCVF; and
  c) a nucleotide sequence encoding a furin cleavage marker located downstream of the signal peptide-encoding nucleotide sequence and upstream of the RdCVF-encoding nucleotide sequence, wherein the signal peptide-encoding sequence and the furin cleavage marker sequence are separated by a nucleotide sequence encoding SEQ ID NO:1.

9. A mammalian cell comprising an expression vector for expression of rod-derived cone viability factor (RdCVF) in a cell, said vector comprising:
  a) a RdCVF-encoding nucleotide sequence;
  b) a signal peptide-encoding nucleotide sequence positioned upstream of the RdCVF-encoding nucleotide sequence, wherein the signal peptide-encoding sequence encodes the signal peptide of insulin growth factor-1 (IGF-1) and directs secretion of expressed RdCVF; and
  c) a nucleotide sequence encoding a furin cleavage marker located downstream of the signal peptide-encoding nucleotide sequence and upstream of the RdCVF-encoding nucleotide sequence, wherein the signal peptide-encoding sequence and the furin cleavage marker sequence are separated by a nucleotide sequence encoding SEQ ID NO:1.

10. The cell of claim 9, wherein the RdCVF-encoding nucleotide sequence lacks the initiating methionine coding sequence.

11. A method for expressing of rod-derived cone viability factor (RdCVF), in a host cell, wherein said method comprises:
  providing a mammalian cell comprising a RdCVF expression vector, wherein the vector comprises:
    a) a RdCVF-encoding nucleotide sequence;
    b) a signal peptide-encoding nucleotide sequence positioned upstream of the RdCVF-encoding nucleotide sequence, wherein the signal peptide-encoding sequence encodes the signal peptide of insulin growth factor-1 (IGF-1); and
    c) a nucleotide sequence encoding a furin cleavage marker located downstream of the signal peptide-encoding nucleotide sequence and immediately upstream of the RdCVF-encoding nucleotide sequence, wherein the signal peptide-encoding sequence and the furin cleavage marker sequence are separated by a nucleotide sequence encoding SEQ ID NO: 1; and
  culturing the mammalian cell under conditions such that RdCVF is expressed.

12. The method of claim 11, wherein the RdCVF-encoding nucleotide sequence lacks the initiating methionine coding sequence.

13. The method of claim 11, wherein the mammalian cell is a CHO cell or a COS cell.

14. The method of claim 11, wherein the RdCVF-encoding nucleotide sequence encodes the long form of RdCVF.

15. The method of claim 11, wherein the nucleotide sequence the furin cleavage marker is a sequence encoding the amino acid sequence KRIKR.

16. The method of claim 11, further comprising the step of isolating the expressed RdCVF protein.

* * * * *

SEQUENCE LISTING

<160> NUMBER OF SEQ ID NOS: 33

<210> SEQ ID NO 1
<211> LENGTH: 19
<212> TYPE: PRT
<213> ORGANISM: Artificial Sequence
<220> FEATURE:
<223> OTHER INFORMATION: Amino acid linker

<400> SEQUENCE: 1

Met Pro Leu Glu Ser Gly Leu Ser Ser Glu Asp Ser Ala Ser Ser Glu
1               5                   10                  15

Ser Phe Ala

<210> SEQ ID NO 2
<211> LENGTH: 5
<212> TYPE: PRT
<213> ORGANISM: Artificial Sequence
<220> FEATURE:
<223> OTHER INFORMATION: Furin cleavage marker

<400> SEQUENCE: 2

Lys Arg Ile Lys Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Furin cleavage sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 3

Arg Xaa Lys Arg Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Furin cleavage marker
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 4

Xaa Arg Xaa Lys Arg Arg
1               5

<210> SEQ ID NO 5
<211> LENGTH: 12
<212> TYPE: PRT
<213> ORGANISM: Artificial Sequence
<220> FEATURE:
<223> OTHER INFORMATION: amino acid tag

<400> SEQUENCE: 5

Glu Asp Gln Val Asp Pro Arg Leu Ile Asp Gly Lys

<210> SEQ ID NO 6
<211> LENGTH: 260
<212> TYPE: PRT
<213> ORGANISM: Artificial Sequence
<220> FEATURE:
<223> OTHER INFORMATION: GUSB signal peptide-furin-RdCVF (LF)

<400> SEQUENCE: 6

Met Ala Arg Gly Ser Ala Val Ala Trp Ala Ala Leu Gly Pro Leu Leu
1               5                   10                  15

Trp Gly Cys Ala Leu Gly Leu Gln Met Pro Leu Glu Ser Gly Leu Ser
            20                  25                  30

Ser Glu Asp Ser Ala Ser Ser Glu Ser Phe Ala Lys Arg Ile Lys Arg
        35                  40                  45

Met Ala Ser Leu Phe Ser Gly Arg Ile Leu Ile Arg Asn Asn Ser Asp
    50                  55                  60

Gln Asp Glu Leu Asp Thr Glu Ala Glu Val Ser Arg Arg Leu Glu Asn
65                  70                  75                  80

Arg Leu Val Leu Leu Phe Phe Gly Ala Gly Ala Cys Pro Gln Cys Gln
                85                  90                  95

Ala Phe Val Pro Ile Leu Lys Asp Phe Phe Val Arg Leu Thr Asp Glu
            100                 105                 110

Phe Tyr Val Leu Arg Ala Ala Gln Leu Ala Leu Val Tyr Val Ser Gln
        115                 120                 125

Asp Ser Thr Glu Glu Gln Gln Asp Leu Phe Leu Lys Asp Met Pro Lys
    130                 135                 140

Lys Trp Leu Phe Leu Pro Phe Glu Asp Asp Leu Arg Arg Asp Leu Gly
145                 150                 155                 160

Arg Gln Phe Ser Val Glu Arg Leu Pro Ala Val Val Leu Lys Pro
                165                 170                 175

Asp Gly Asp Val Leu Thr Arg Asp Gly Ala Asp Glu Ile Gln Arg Leu
            180                 185                 190

Gly Thr Ala Cys Phe Ala Asn Trp Gln Glu Ala Ala Glu Val Leu Asp
        195                 200                 205

Arg Asn Phe Gln Leu Pro Glu Asp Leu Glu Asp Gln Glu Pro Arg Ser
    210                 215                 220

Leu Thr Glu Cys Leu Arg Arg His Lys Tyr Arg Val Glu Lys Ala Ala
225                 230                 235                 240

Arg Gly Gly Arg Asp Pro Gly Gly Gly Gly Glu Glu Gly Gly Ala
                245                 250                 255

Gly Gly Leu Phe
            260

<210> SEQ ID NO 7
<211> LENGTH: 1101
<212> TYPE: DNA
<213> ORGANISM: Artificial Sequence
<220> FEATURE:
<223> OTHER INFORMATION: GUSB signal peptide-furin-RdCVF(LF)

<400> SEQUENCE: 7
gaattcctcc ggggaccaca cgccgcgctg tccccagcac ttaccatggc ccggggtcg      60 gcggttgcct gggcggcgct cgggccgttg ttgtggggct gcgcgctggg gctgcagatg    120
cccctcgagt ccggccttgct gtcctccgag gactccgcca gctccgagag cttcgccaag   180

```
cgcatcaagc gcatggcctc cctgttctct ggccgcatcc tgatccgcaa caatagcgac      240
caggacgagc tggatacgga ggctgaggtc agtcgcaggc tggagaaccg gctggtgctg      300
ctgttctttg gtgctggggc ttgtccacag tgccaggcct tcgtgcccat cctcaaggac      360
ttcttcgtgc ggctcacaga tgagttctat gtactgcggg cggctcagct ggccctggtg      420
tacgtgtccc aggactccac ggaggagcag caggacctgt tcctcaagga catgccaaag      480
aaatggcttt tcctgccctt tgaggatgat ctgaggaggg acctcgggcg ccagttctca      540
gtggagcgcc tgccggcggt cgtggtgctc aagccggacg gggacgtgct cactcgcgac      600
ggcgccgacg agatccagcg cctgggcacc gcctgcttcg ccaactggca ggaggcggcc      660
gaggtgctgg accgcaactt ccagctgcca gaggacctgg aggaccagga gccacggagc      720
ctcaccgagt gcctgcgccg ccacaagtac cgcgtggaaa aggcggcgcg aggcgggcgc      780
gacccggggg gaggggtgg ggaggagggc ggggccgggg ggctgttctg acccgctagg      840
gtggaggaga ggagtggggt tgttgatga acctccaccc ccaccccacc ccgcacgcc       900 tgtaatccca gcacttgggg aggccaaggc gggaggatcg cttgagccca gaggttcgag      960
atcaacctgg gcaagagagt gagaccctga ctctacgaaa attaaaagtt agcccggtgt     1020
ggtggcgcgc acctgtggct tagctacccct gaaaaaaaaa aaaaaaaaaa aaaaaaaaa     1080 aaaaaaaaaa aaaaagcttc c                                              1101
```

<210> SEQ ID NO 8
<211> LENGTH: 255
<212> TYPE: PRT
<213> ORGANISM: Artificial Sequence
<220> FEATURE:
<223> OTHER INFORMATION: BDNF signal peptide-furin-RdCVF(LF)

<400> SEQUENCE: 8

```
Met Thr Ile Leu Phe Leu Thr Met Val Ile Ser Tyr Phe Gly Cys Met
 1               5                  10                  15

Lys Ala Ala Pro Met Pro Leu Glu Ser Gly Leu Ser Ser Glu Asp Ser
            20                  25                  30

Ala Ser Ser Glu Ser Phe Ala Lys Arg Ile Lys Arg Met Ala Ser Leu
        35                  40                  45

Phe Ser Gly Arg Ile Leu Ile Arg Asn Asn Ser Asp Gln Asp Glu Leu
    50                  55                  60

Asp Thr Glu Ala Glu Val Ser Arg Arg Leu Glu Asn Arg Leu Val Leu
65                  70                  75                  80

Leu Phe Phe Gly Ala Gly Ala Cys Pro Gln Cys Gln Ala Phe Val Pro
                85                  90                  95

Ile Leu Lys Asp Phe Phe Val Arg Leu Thr Asp Glu Phe Tyr Val Leu
            100                 105                 110

Arg Ala Ala Gln Leu Ala Leu Val Tyr Val Ser Gln Asp Ser Thr Glu
        115                 120                 125

Glu Gln Gln Asp Leu Phe Leu Lys Asp Met Pro Lys Lys Trp Leu Phe
    130                 135                 140

Leu Pro Phe Glu Asp Asp Leu Arg Arg Asp Leu Gly Arg Gln Phe Ser
145                 150                 155                 160

Val Glu Arg Leu Pro Ala Val Val Leu Lys Pro Asp Gly Asp Val
                165                 170                 175

Leu Thr Arg Asp Gly Ala Asp Glu Ile Gln Arg Leu Thr Ala Cys Phe
            180                 185                 190

Ala Asn Trp Gln Glu Ala Ala Glu Val Leu Asp Arg Asn Phe Gln Leu
```

```
                     195                 200                 205
Pro Glu Asp Leu Glu Asp Gln Glu Pro Arg Ser Leu Thr Glu Cys Leu
    210                 215                 220

Arg Arg His Lys Tyr Arg Val Glu Lys Ala Ala Arg Gly Gly Arg Asp
225                 230                 235                 240

Pro Gly Gly Gly Gly Glu Glu Gly Gly Ala Gly Gly Leu Phe
                245                 250                 255

<210> SEQ ID NO 9
<211> LENGTH: 1085
<212> TYPE: DNA
<213> ORGANISM: Artificial Sequence
<220> FEATURE:
<223> OTHER INFORMATION: BDNF signal peptide-furin-RdCVF(LF)

<400> SEQUENCE: 9
gaattcctcc ggggaccaca cgccgcgctg tccccagcac ttaccatgac catccttttc      60
cttactatgg ttatttcata ctttggttgc atgaaggctg cccccatgcc cctcgagtcc     120
ggcctgtcct ccgaggactc cgccagctcc gagagcttcg ccaagcgcat caagcgcatg     180 gcctcccctgt tctctggccg catcctgatc cgcaacaata gcgaccagga cgagctggat     240
acggaggctg aggtcagtcg caggctggag aaccggctgg tgctgctgtt ctttggtgct     300
ggggcttgtc cacagtgcca ggccttcgtg cccatcctca aggacttctt cgtgcggctc     360
acagatgagt tctatgtact gcgggcggct cagctggccc tggtgtacgt gtcccaggac     420
tccacggagg agcagcagga cctgttcctc aaggacatgc caaagaaatg cttttcctg     480 cccctttgagg atgatctgag gagggacctc gggcgccagt tctcagtgga gcgcctgccg     540
gcggtcgtgg tgctcaagcc ggacggggac gtgctcactc gcgacggcgc cgacgagatc     600
cagcgcctgg gcaccgcctg cttcgccaac tggcaggagg cggccgaggt gctggaccgc     660
aacttccagc tgccagagga cctggaggac caggagccac ggagcctcac cgagtgcctg     720
cgccgccaca gtaccgcgt ggaaaaggcg gcgcgaggcg ggcgcgaccc cgggggaggg     780
ggtggggagg agggcggggc cggggggctg ttctgacccg ctagggtgga ggagaggagt     840
ggggtttgtt gatgaacctc cacccccacc ccaccccgc acgcctgtaa tcccagcact     900
tggggaggcc aaggcgggag gatcgcttga gcccagaggt tcgagatcaa cctgggcaag     960
agagtgagac cctgactcta cgaaaattaa aagttagccc ggtgtggtgg cgcgcacctg    1020
tggcttagct accctgaaaa aaaaaaaaa aaaaaaaaa aaaaaaaaa aaaaaaaaa       1080 gcttg                                                                1085

<210> SEQ ID NO 10
<211> LENGTH: 286
<212> TYPE: PRT
<213> ORGANISM: Artificial Sequence
<220> FEATURE:
<223> OTHER INFORMATION: IGF-1 signal peptide-furin-RdCVF(LF)

<400> SEQUENCE: 10

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
                20                  25                  30

Phe Tyr Leu Ala Leu Cys Leu Leu Thr Phe Thr Ser Ser Ala Thr Ala
            35                  40                  45

Gly Pro Met Pro Leu Glu Ser Gly Leu Ser Ser Glu Asp Ser Ala Ser
```

```
            50                  55                  60
Ser Glu Ser Phe Ala Lys Arg Ile Lys Arg Met Ala Ser Leu Phe Ser
 65                  70                  75                  80

Gly Arg Ile Leu Ile Arg Asn Asn Ser Asp Gln Asp Glu Leu Asp Thr
                 85                  90                  95

Glu Ala Glu Val Ser Arg Arg Leu Glu Asn Arg Leu Val Leu Leu Phe
            100                 105                 110

Phe Gly Ala Gly Ala Cys Pro Gln Cys Gln Ala Phe Val Pro Ile Leu
            115                 120                 125

Lys Asp Phe Phe Val Arg Leu Thr Asp Glu Phe Tyr Val Leu Arg Ala
        130                 135                 140

Ala Gln Leu Ala Leu Val Tyr Val Ser Gln Asp Ser Thr Glu Glu Gln
145                 150                 155                 160

Gln Asp Leu Phe Leu Lys Asp Met Pro Lys Lys Trp Leu Phe Leu Pro
                165                 170                 175

Phe Glu Asp Asp Leu Arg Arg Asp Leu Gly Arg Gln Phe Ser Val Glu
            180                 185                 190

Arg Leu Pro Ala Val Val Val Leu Lys Pro Asp Gly Asp Val Leu Thr
        195                 200                 205

Arg Asp Gly Ala Asp Glu Ile Gln Arg Leu Gly Thr Ala Cys Phe Ala
    210                 215                 220

Asn Trp Gln Glu Ala Ala Glu Val Leu Asp Arg Asn Phe Gln Leu Pro
225                 230                 235                 240

Glu Asp Leu Glu Asp Gln Glu Pro Arg Ser Leu Thr Glu Cys Leu Arg
                245                 250                 255

Arg His Lys Tyr Arg Val Glu Lys Ala Ala Arg Gly Gly Arg Asp Pro
            260                 265                 270

Gly Gly Gly Gly Gly Glu Glu Gly Gly Ala Gly Gly Leu Phe
        275                 280                 285

<210> SEQ ID NO 11
<211> LENGTH: 1178
<212> TYPE: DNA
<213> ORGANISM: Artificial Sequence
<220> FEATURE:
<223> OTHER INFORMATION: IGF-1 signal peptide-furin-RdCVF(LF)

<400> SEQUENCE: 11
gaattcctcc ggggaccaca cgccgcgctg tccccagcac ttaccatggg aaaaatcagc      60
agtcttccaa cccaattatt taagtgctgc ttttgtgatt tcttgaaggt gaagatgcac     120
accatgtcct cctcgcatct cttctacctg gcgctgtgcc tgctcacctt caccagctct     180
gccacggctg accggagat gccccctcgag tccggcctgt cctccgagga ctccgccagc     240
tccgagagct cgccaagcg catcaagcgc atggcctccc tgttctctgg ccgcatcctg     300
atccgcaaca atagcgacca ggacgagctg gatacggagg ctgaggtcag tcgcaggctg     360
gagaaccggc tggtgctgct gttctttggt gctgggcctt gtccacagtg ccaggccttc     420
gtgcccatcc tcaaggactt cttcgtgcgg ctcacagatg agttctatgt actgcgggcg     480
gctcagctgg ccctggtgta cgtgtcccag gactccacgg aggagcagca ggacctgttc     540
ctcaaggaca tgccaaagaa atggcttttc ctgccctttg aggatgatct gaggagggac     600
ctcgggcgcc agttctcagt ggagcgcctg ccggcggtcg tggtgctcaa gccggacggg     660
gacgtgctca ctcgcgacgg cgccgacgag atccagcgcc tgggcaccgc tgcttcgcc     720 aactggcagg aggcggccga ggtgctggac cgcaacttcc agctgccaga ggacctggag     780
```

```
gaccaggagc cacggagcct caccgagtgc ctgcgccgcc acaagtaccg cgtggaaaag    840
gcggcgcgag gcgggcgcga ccccggggga gggggtgggg aggagggcgg ggccgggggg    900
ctgttctgac ccgctagggt ggaggagagg agtggggttt gttgatgaac ctccaccccc    960
accccacccc cgcacgcctg taatcccagc acttggggag gccaaggcgg gaggatcgct   1020
tgagcccaga ggttcgagat caacctgggc aagagagtga gaccctgact ctacgaaaat   1080
taaaagttag cccggtgtgg tggcgcgcac ctgtggctta gctaccctga aaaaaaaaa    1140 aaaaaaaaa aaaaaaaaa aaaaaaaaa aaagcttc                              1178

<210> SEQ ID NO 12
<211> LENGTH: 157
<212> TYPE: PRT
<213> ORGANISM: Artificial Sequence
<220> FEATURE:
<223> OTHER INFORMATION: GUSB signal peptide-furin-RdCVF(SF)

<400> SEQUENCE: 12

Met Ala Arg Gly Ser Ala Val Ala Trp Ala Ala Leu Gly Pro Leu Leu
1               5                   10                  15

Trp Gly Cys Ala Leu Gly Leu Gln Met Pro Leu Glu Ser Gly Leu Ser
            20                  25                  30

Ser Glu Asp Ser Ala Ser Ser Glu Ser Phe Ala Lys Arg Ile Lys Arg
        35                  40                  45

Met Ala Ser Leu Phe Ser Gly Arg Ile Leu Ile Arg Asn Asn Ser Asp
    50                  55                  60

Gln Asp Glu Leu Asp Thr Glu Ala Glu Val Ser Arg Arg Leu Glu Asn
65                  70                  75                  80

Arg Leu Val Leu Leu Phe Phe Gly Ala Gly Ala Cys Pro Gln Cys Gln
                85                  90                  95

Ala Phe Val Pro Ile Leu Lys Asp Phe Phe Val Arg Leu Thr Asp Glu
            100                 105                 110

Phe Tyr Val Leu Arg Ala Ala Gln Leu Ala Leu Val Tyr Val Ser Gln
        115                 120                 125

Asp Ser Thr Glu Glu Gln Gln Asp Leu Phe Leu Lys Asp Met Pro Lys
    130                 135                 140

Lys Trp Leu Phe Leu Pro Phe Glu Asp Asp Leu Arg Arg
145                 150                 155

<210> SEQ ID NO 13
<211> LENGTH: 616
<212> TYPE: DNA
<213> ORGANISM: Artificial Sequence
<220> FEATURE:
<223> OTHER INFORMATION: GUSB signal peptide-furin-RdCVF(SF)

<400> SEQUENCE: 13
gaattcctcc ggggaccaca cgccgcgctg tccccagcac ttaccatggc ccggggtcg     60 gcggttgcct gggcggcgct cgggccgttg ttgtggggct gcgcgctggg gctgcagatg   120
cccctcgagt ccggcttgct gtcctccgag gactccgcca gctccgagag cttcgccaag   180
cgcatcaagc gcatggcctc cctgttctct ggccgcatcc tgatccgcaa caatagcgac   240
caggacgagc tggatacgga ggctgaggtc agtcgcaggc tggagaaccg gctggtgctg   300
ctgttctttg gtgctgggc ttgtccacag tgccaggcct cgtgcccat cctcaaggac    360 ttcttcgtgc ggctcacaga tgagttctat gtactgcggg cggctcagct ggccctggtg   420
```

```
tacgtgtccc aggactccac ggaggagcag caggacctgt cctcaagga catgccaaag    480 aaatggcttt tcctgccctt tgaggatgat ctgaggaggt gaggcccag ggaagaccag    540 ggagggcttc ctggagaagg catttccctg gaggtttact gtcctggtac tacttgtgca    600
taaagaggta aagctt                                                    616
```

<210> SEQ ID NO 14
<211> LENGTH: 153
<212> TYPE: PRT
<213> ORGANISM: Artificial Sequence
<220> FEATURE:
<223> OTHER INFORMATION: BDNF signal peptide-furin-RdCVF(SF)

<400> SEQUENCE: 14

```
Met Thr Ile Leu Phe Leu Thr Met Val Ile Ser Tyr Phe Gly Cys Met
1               5                   10                  15

Lys Ala Ala Pro Met Pro Leu Glu Ser Gly Leu Ser Ser Glu Asp Ser
                20                  25                  30

Ala Ser Ser Glu Ser Phe Ala Lys Arg Ile Lys Arg Met Ala Ser Leu
            35                  40                  45

Phe Ser Gly Arg Ile Leu Ile Arg Asn Asn Ser Asp Gln Asp Glu Leu
    50                  55                  60

Asp Thr Glu Ala Glu Val Ser Arg Arg Leu Glu Asn Arg Leu Val Leu
65                  70                  75                  80

Leu Phe Phe Gly Ala Gly Ala Cys Pro Gln Cys Gln Ala Phe Val Pro
                85                  90                  95

Ile Leu Lys Asp Phe Phe Val Arg Leu Thr Asp Glu Phe Tyr Val Leu
                100                 105                 110

Arg Ala Ala Gln Leu Ala Leu Val Tyr Val Ser Gln Asp Ser Thr Glu
            115                 120                 125

Glu Gln Gln Asp Leu Phe Leu Lys Asp Met Pro Lys Lys Trp Leu Phe
    130                 135                 140

Leu Pro Phe Glu Asp Asp Leu Arg Arg
145                 150
```

<210> SEQ ID NO 15
<211> LENGTH: 601
<212> TYPE: DNA
<213> ORGANISM: Artificial Sequence
<220> FEATURE:
<223> OTHER INFORMATION: BDNF signal peptide-furin-RdCVF(SF)

<400> SEQUENCE: 15

```
gaattcctcc ggggaccaca cgccgcgctg tccccagcac ttaccatgac catccttttc     60
cttactatgg ttatttcata ctttggttgc atgaaggctg cccccatgcc cctcgagtcc    120
ggcctgtcct ccgaggactc cgccagctcc gagagcttcg ccaagcgcat caagcgcatg    180
gcctccctgt tctctggccg catcctgatc cgcaacaata gcgaccagga cgagctggat    240
acggaggctg aggtcagtcg caggctggag aaccggctgg tgctgctgtt ctttggtgct    300
ggggcttgtc cacagtgcca ggccttcgtg cccatcctca aggacttctt cgtgcggctc    360
acagatgagt tctatgtact gcgggcggct cagctggccc tggtgtacgt gtcccaggac    420
tccacggagg agcagcagga cctgttcctc aaggacatgc caaagaaatg gcttttcctg    480
ccctttgagg atgatctgag gaggtgaggc ccagggaag accagggagg cttcctgga    540 gaaggcattt ccctggaggt ttactgtcct ggtactactt gtgcataaag aggtaaagct    600
t                                                                     601
```

<210> SEQ ID NO 16
<211> LENGTH: 183
<212> TYPE: PRT
<213> ORGANISM: Artificial Sequence
<220> FEATURE:
<223> OTHER INFORMATION: IGF1 signal peptide-furin-RdCVF(SF)

<400> SEQUENCE: 16

```
Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Gly Pro Met Pro Leu Glu Ser Gly Leu Ser Ser Glu Asp Ser Ala Ser
    50                  55                  60

Ser Glu Ser Phe Ala Lys Arg Ile Lys Arg Met Ala Ser Leu Phe Ser
65                  70                  75                  80

Gly Arg Ile Leu Ile Arg Asn Asn Ser Asp Gln Asp Glu Leu Asp Thr
                85                  90                  95

Glu Ala Glu Val Ser Arg Arg Leu Glu Asn Arg Leu Val Leu Leu Phe
            100                 105                 110

Phe Gly Ala Gly Ala Cys Pro Gln Cys Gln Ala Phe Val Pro Ile Leu
        115                 120                 125

Lys Asp Phe Phe Val Arg Leu Thr Asp Glu Phe Tyr Val Leu Arg Ala
    130                 135                 140

Ala Gln Leu Ala Leu Val Tyr Val Ser Gln Asp Ser Thr Glu Glu Gln
145                 150                 155                 160

Gln Asp Leu Phe Leu Lys Asp Met Pro Lys Lys Trp Leu Phe Leu Pro
                165                 170                 175

Phe Glu Asp Asp Leu Arg Arg
            180
```

<210> SEQ ID NO 17
<211> LENGTH: 694
<212> TYPE: DNA
<213> ORGANISM: Artificial Sequence
<220> FEATURE:
<223> OTHER INFORMATION: IGF1 signal peptide-furin-RdCVF(SF)

<400> SEQUENCE: 17

```
gaattcctcc ggggaccaca cgccgcgctg tccccagcac ttaccatggg aaaaatcagc    60
agtcttccaa cccaattatt taagtgctgc ttttgtgatt tcttgaaggt gaagatgcac   120
accatgtcct cctcgcatct cttctacctg gcgctgtgcc tgctcacctt caccagctct   180
gccacggctg gaccggagat gcccctcgag tccggcctgt cctccgagga ctccgccagc   240
tccgagagct cgccaagcg catcaagcgc atggcctccc tgttctctgg ccgcatcctg   300
atccgcaaca atagcgacca ggacgagctg atacgagg ctgaggtcag tcgcaggctg   360
gagaaccggc tggtgctgct gttctttggt gctgggggctt gtccacagtg ccaggccttc   420
gtgcccatcc tcaaggactt cttcgtgcgc ctcacagatg agttctatgt actgcgggcg   480
gctcagctgg ccctggtgta cgtgtcccag gactccacgg aggagcagca ggacctgttc   540
ctcaaggaca tgccaaagaa atggcttttc ctgccctttg aggatgatct gaggaggtga   600
ggccccaggg aagaccaggg agggcttcct ggagaaggca tttccctgga ggtttactgt   660
```
cctggtacta cttgtgcata aagaggtaaa gctt                                694

<210> SEQ ID NO 18
<211> LENGTH: 714
<212> TYPE: DNA
<213> ORGANISM: Artificial Sequence
<220> FEATURE:
<223> OTHER INFORMATION: human growth hormone signal peptide-RdCVF(LF)

<400> SEQUENCE: 18
atggctacag gctcccggac gtccctgctc ctggcttttg gcctgctctg cctcccctgg    60
cttcaagagg gatccgccgc ctccctgttc tctggccgca tcctgatccg caacaatagc   120
gaccaggacg agctggatac ggaggctgag gtcagtcgca ggctggagaa ccggctggtg   180
ctgctgttct tggtgctggg gcttgtccca cagtgccagg ccttcgtgcc catcctcaag   240
gacttcttcg tgcggctcac agatgagttc tatgtactgc gggcggctca gctggccctg   300
gtgtacgtgt cccaggactc cacggaggag cagcaggacc tgttcctcaa ggacatgcca   360
aagaaatggc ttttcctgcc ctttgaggat gatctgagga gggaccctcg gcgccagttc   420
tcagtggagc gcctgccggc ggtcgtggtg ctcaagccgg acggggacgt gctcactcgc   480
gacggcgccg acgagatcca gcgcctgggc accgcctgct cgccaactg gcaggaggcg   540
gccgaggtgc tggaccgcaa cttccagctg ccagaggacc tggaggacca ggagccacgg   600
agcctcaccg agtgcctgcg ccgccacaag taccgcgtgg aaaaggcggc gcgaggcggg   660
cgcgaccccg ggggaggggg tggggaggag ggcggggccg ggggctgtt ctga           714

<210> SEQ ID NO 19
<211> LENGTH: 236
<212> TYPE: PRT
<213> ORGANISM: Artificial Sequence
<220> FEATURE:
<223> OTHER INFORMATION: human growth hormone signal peptide-RdCVF(LF)

<400> SEQUENCE: 19

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Ser Leu Phe Ser Gly
            20                  25                  30

Arg Ile Leu Ile Arg Asn Asn Ser Asp Gln Asp Glu Leu Asp Thr Glu
        35                  40                  45

Ala Glu Val Ser Arg Arg Leu Glu Asn Arg Leu Val Leu Leu Phe Phe
    50                  55                  60

Gly Ala Gly Ala Cys Pro Gln Cys Gln Ala Phe Val Pro Ile Leu Lys
65                  70                  75                  80

Asp Phe Phe Val Arg Leu Thr Asp Glu Tyr Val Leu Arg Ala Ala Gln
                85                  90                  95

Leu Ala Leu Val Tyr Val Ser Gln Asp Ser Thr Glu Glu Gln Gln Asp
            100                 105                 110

Leu Phe Leu Lys Asp Met Pro Lys Lys Trp Leu Phe Leu Pro Phe Glu
        115                 120                 125

Asp Asp Leu Arg Arg Asp Leu Gly Arg Gln Phe Ser Val Glu Arg Leu
    130                 135                 140

Pro Ala Val Val Val Leu Lys Pro Asp Gly Asp Val Leu Thr Arg Asp
145                 150                 155                 160

Gly Ala Asp Glu Ile Gln Arg Leu Gly Thr Ala Cys Phe Ala Asn Trp
                165                 170                 175

-continued

```
Gln Glu Ala Ala Glu Val Leu Asp Arg Asn Phe Gln Leu Pro Glu Asp
            180                 185                 190

Leu Glu Asp Gln Glu Pro Arg Ser Leu Thr Glu Cys Leu Arg Arg His
        195                 200                 205

Lys Tyr Arg Val Glu Lys Ala Ala Arg Gly Gly Arg Asp Pro Gly Gly
    210                 215                 220

Gly Gly Gly Glu Glu Gly Gly Ala Gly Gly Leu Phe
225                 230                 235

<210> SEQ ID NO 20
<211> LENGTH: 405
<212> TYPE: DNA
<213> ORGANISM: Artificial Sequence
<220> FEATURE:
<223> OTHER INFORMATION: growth hormone signal peptide - RdCVF(SF)

<400> SEQUENCE: 20
atggctacag ctcccggac gtccctgctc ctggcttttg gcctgctctg cctcccctgg      60
cttcaagagg gatccgccgc ctccctgttc tctggccgca tcctgatccg caacaatagc     120
gaccaggacg agctggatac ggaggctgag gtcagtcgca ggctggagaa ccggctggtg     180
ctgctgttct tggtgctgg ggcttgtcca cagtgccagg ccttcgtgcc catcctcaag      240
gacttcttcg tgcggctcac agatgagttc tatgtactgc gggcggctca gctggccctg     300
gtgtacgtgt cccaggactc cacggaggag cagcaggacc tgttcctcaa ggacatgcca     360
aagaaatggc ttttcctgcc ctttgaggat gatctgagga ggtga                     405

<210> SEQ ID NO 21
<211> LENGTH: 133
<212> TYPE: PRT
<213> ORGANISM: Artificial Sequence
<220> FEATURE:
<223> OTHER INFORMATION: hGH signal peptide - RdCVF(SF)

<400> SEQUENCE: 21

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Ser Leu Phe Ser Gly
            20                  25                  30

Arg Ile Leu Ile Arg Asn Asn Ser Asp Gln Asp Glu Leu Asp Thr Glu
        35                  40                  45

Ala Glu Val Ser Arg Arg Leu Glu Asn Arg Leu Val Leu Leu Phe Phe
    50                  55                  60

Gly Ala Gly Ala Cys Pro Gln Cys Gln Ala Phe Val Pro Ile Leu Lys
65                  70                  75                  80

Asp Phe Phe Val Arg Leu Thr Asp Glu Phe Tyr Leu Arg Ala Ala Gln
                85                  90                  95

Leu Ala Leu Val Tyr Val Ser Gln Asp Ser Thr Glu Glu Gln Gln Asp
            100                 105                 110

Leu Phe Leu Lys Asp Met Pro Lys Lys Trp Leu Phe Leu Pro Phe Glu
        115                 120                 125

Asp Asp Leu Arg Arg
    130

<210> SEQ ID NO 22
<211> LENGTH: 750
<212> TYPE: DNA
<213> ORGANISM: Artificial Sequence
<220> FEATURE:
```

<223> OTHER INFORMATION: hGH signal peptide - RdCVF(LF)-HPC4

<400> SEQUENCE: 22

```
atggctacag gctcccggac gtccctgctc ctggcttttg gcctgctctg cctcccctgg      60
cttcaagagg gatccgccgc ctccctgttc tctggccgca tcctgatccg caacaatagc     120
gaccaggacg agctggatac ggaggctgag gtcagtcgca ggctggagaa ccggctggtg     180
ctgctgttct tggtgctggg gcttgtcca cagtgccagg ccttcgtgcc catcctcaag      240
gacttcttcg tgcggctcac agatgagttc tatgtactgc gggcggctca gctggccctg     300
gtgtacgtgt cccaggactc cacggaggag cagcaggacc tgttcctcaa ggacatgcca     360
aagaaatggc ttttcctgcc ctttgaggat gatctgagga gggacctcgg gcgccagttc     420
tcagtggagc gcctgccggc ggtcgtggtg ctcaagccgg acggggacgt gctcactcgc     480
gacggcgccg acgagatcca gcgcctgggc accgcctgct cgccaactg gcaggaggcg     540
gccgaggtgc tggaccgcaa cttccagctg ccagaggacc tggaggacca ggagccacgg     600
agcctcaccg agtgcctgcg ccgccacaag taccgcgtgg aaaaggcggc gcgaggcggg     660
cgcgaccccg ggggagggggg tggggaggag ggcggggccg gggggctgtt cgaagatcaa     720
gtcgatccac gcctcatcga tggcaaatga                                       750
```

<210> SEQ ID NO 23
<211> LENGTH: 248
<212> TYPE: PRT
<213> ORGANISM: Artificial Sequence
<220> FEATURE:
<223> OTHER INFORMATION: hGH signal peptide - RdCVF(LF)-HPC4

<400> SEQUENCE: 23

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Ser Leu Phe Ser Gly
                20                  25                  30

Arg Ile Leu Ile Arg Asn Asn Ser Asp Gln Asp Glu Leu Asp Thr Glu
            35                  40                  45

Ala Glu Val Ser Arg Arg Leu Glu Asn Arg Leu Val Leu Leu Phe Phe
        50                  55                  60

Gly Ala Gly Ala Cys Pro Gln Cys Gln Ala Phe Val Pro Ile Leu Lys
65                  70                  75                  80

Asp Phe Phe Val Arg Leu Thr Asp Glu Tyr Val Leu Arg Ala Ala Gln
                85                  90                  95

Leu Ala Leu Val Tyr Val Ser Gln Asp Ser Thr Glu Glu Gln Gln Asp
            100                 105                 110

Leu Phe Leu Lys Asp Met Pro Lys Lys Trp Leu Phe Leu Pro Phe Glu
        115                 120                 125

Asp Asp Leu Arg Arg Asp Leu Gly Arg Gln Phe Ser Val Glu Arg Leu
130                 135                 140

Pro Ala Val Val Val Leu Lys Pro Asp Gly Asp Val Leu Thr Arg Asp
145                 150                 155                 160

Gly Ala Asp Glu Ile Gln Arg Leu Gly Thr Ala Cys Phe Ala Asn Trp
                165                 170                 175

Gln Glu Ala Ala Glu Val Leu Asp Arg Asn Phe Gln Leu Pro Glu Asp
            180                 185                 190

Leu Glu Asp Gln Glu Pro Arg Ser Leu Thr Glu Cys Leu Arg Arg His
        195                 200                 205
```

```
Lys Tyr Arg Val Glu Lys Ala Ala Arg Gly Gly Arg Asp Pro Gly Gly
    210                 215                 220

Gly Gly Gly Glu Glu Gly Ala Gly Gly Leu Phe Glu Asp Gln Val
225                 230                 235                 240

Asp Pro Arg Leu Ile Asp Gly Lys
                245

<210> SEQ ID NO 24
<211> LENGTH: 441
<212> TYPE: DNA
<213> ORGANISM: Artificial Sequence
<220> FEATURE:
<223> OTHER INFORMATION: hGH signal peptide - RdCVF(SF)-HPC4

<400> SEQUENCE: 24
atggctacag gctcccggac gtccctgctc ctggcttttg gcctgctctg cctcccctgg      60
cttcaagagg gatccgccgc tccctgttc tctggccgca tcctgatccg caacaatagc     120
gaccaggacg agctggatac ggaggctgag gtcagtcgca ggctggagaa ccggctggtg     180
ctgctgttct ttggtgctgg gcttgtcca cagtgccagg ccttcgtgcc atcctcaag      240 gacttcttcg tgcggctcac agatgagttc tatgtactgc gggcggctca gctggccctg     300
gtgtacgtgt cccaggactc cacggaggag cagcaggacc tgttcctcaa ggacatgcca     360
aagaaatggc ttttcctgcc ctttgaggat gatctgagga gggaagatca agtcgatcca     420
cgcctcatcg atggcaaatg a                                              441

<210> SEQ ID NO 25
<211> LENGTH: 145
<212> TYPE: PRT
<213> ORGANISM: Artificial Sequence
<220> FEATURE:
<223> OTHER INFORMATION: hGH signal peptide - RdCVF(SF)-HPC4

<400> SEQUENCE: 25

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ala Ser Leu Phe Ser Gly
            20                  25                  30

Arg Ile Leu Ile Arg Asn Asn Ser Asp Gln Asp Glu Leu Asp Thr Glu
        35                  40                  45

Ala Glu Val Ser Arg Arg Leu Glu Asn Arg Leu Val Leu Leu Phe Phe
    50                  55                  60

Gly Ala Gly Ala Cys Pro Gln Cys Gln Ala Phe Val Pro Ile Leu Lys
65                  70                  75                  80

Asp Phe Phe Val Arg Leu Thr Asp Glu Phe Tyr Leu Arg Ala Ala Gln
                85                  90                  95

Leu Ala Leu Val Tyr Val Ser Gln Asp Ser Thr Glu Glu Gln Gln Asp
            100                 105                 110

Leu Phe Leu Lys Asp Met Pro Lys Lys Trp Leu Phe Leu Pro Phe Glu
        115                 120                 125

Asp Asp Leu Arg Arg Glu Asp Gln Val Asp Pro Arg Leu Ile Asp Gly
    130                 135                 140

Lys
145

<210> SEQ ID NO 26
<211> LENGTH: 212
<212> TYPE: PRT
```

<213> ORGANISM: Homo sapiens

<400> SEQUENCE: 26

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg Asp Leu Gly
            100                 105                 110

Arg Gln Phe Ser Val Glu Arg Leu Pro Ala Val Val Leu Lys Pro
        115                 120                 125

Asp Gly Asp Val Leu Thr Arg Asp Gly Ala Asp Glu Ile Gln Arg Leu
    130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
            180                 185                 190

Arg Gly Gly Arg Asp Pro Gly Gly Gly Gly Glu Gly Gly Gly Ala
        195                 200                 205

Gly Gly Leu Phe
    210

<210> SEQ ID NO 27
<211> LENGTH: 109
<212> TYPE: PRT
<213> ORGANISM: Homo sapiens

<400> SEQUENCE: 27

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg
            100                 105

<210> SEQ ID NO 28
<211> LENGTH: 26
<212> TYPE: PRT

<213> ORGANISM: Homo sapiens

<400> SEQUENCE: 28

Met Ala Thr Gly Ser Arg Thr Ser Leu Leu Leu Ala Phe Gly Leu Leu
1               5                   10                  15

Cys Leu Pro Trp Leu Gln Glu Gly Ser Ala
            20                  25

<210> SEQ ID NO 29
<211> LENGTH: 20
<212> TYPE: PRT
<213> ORGANISM: Homo sapiens

<400> SEQUENCE: 29

Met Thr Ile Leu Phe Leu Thr Met Val Ile Ser Tyr Phe Gly Cys Met
1               5                   10                  15

Lys Ala Ala Pro
            20

<210> SEQ ID NO 30
<211> LENGTH: 50
<212> TYPE: PRT
<213> ORGANISM: Homo sapiens

<400> SEQUENCE: 30

Met Gly Lys Ile Ser Ser Leu Pro Thr Gln Leu Phe Lys Cys Cys Phe
1               5                   10                  15

Cys Asp Phe Leu Lys Val Lys Met His Thr Met Ser Ser His Leu
            20                  25                  30

Phe Tyr Leu Ala Leu Cys Leu Leu Thr Phe Thr Ser Ser Ala Thr Ala
            35                  40                  45

Gly Pro
    50

<210> SEQ ID NO 31
<211> LENGTH: 24
<212> TYPE: PRT
<213> ORGANISM: Homo sapiens

<400> SEQUENCE: 31

Met Ala Arg Gly Ser Ala Val Ala Trp Ala Leu Gly Pro Leu Leu
1               5                   10                  15

Trp Gly Cys Ala Leu Gly Leu Gln
            20

<210> SEQ ID NO 32
<211> LENGTH: 212
<212> TYPE: PRT
<213> ORGANISM: Homo sapiens

<400> SEQUENCE: 32

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
            35                  40                  45

Ala Phe Val Pro Ile Leu Lys Asp Phe Phe Val Arg Leu Thr Asp Glu
            50                  55                  60

Phe Tyr Val Leu Arg Ala Ala Gln Leu Ala Leu Val Tyr Val Ser Gln

```
            65                  70                  75                  80
Asp Ser Thr Glu Glu Gln Gln Asp Leu Phe Leu Lys Asp Met Pro Lys
                    85                  90                  95

Lys Trp Leu Phe Leu Pro Phe Glu Asp Asp Leu Arg Arg Asp Leu Gly
                100                 105                 110

Arg Gln Phe Ser Val Glu Arg Leu Pro Ala Val Val Leu Lys Pro
            115                 120                 125

Asp Gly Asp Val Leu Thr Arg Asp Gly Ala Asp Glu Ile Gln Arg Leu
130                 135                 140

Gly Thr Ala Cys Phe Ala Asn Trp Gln Glu Ala Ala Glu Val Leu Asp
145                 150                 155                 160

Arg Asn Phe Gln Leu Pro Glu Asp Leu Glu Asp Gln Glu Pro Arg Ser
                165                 170                 175

Leu Thr Glu Cys Leu Arg Arg His Lys Tyr Arg Val Glu Lys Ala Ala
            180                 185                 190

Arg Gly Gly Arg Asp Pro Gly Gly Gly Gly Glu Glu Gly Ala
            195                 200                 205

Gly Gly Leu Phe
    210

<210> SEQ ID NO 33
<211> LENGTH: 948
<212> TYPE: DNA
<213> ORGANISM: Homo sapiens

<400> SEQUENCE: 33
ccggggacca cacgccgcgc tgtccccagc acccaaccca ggttaccatg gcctccctgt    60
tctctggccg catcctgatc cgcaacaata gcgaccagga cgagctggat acggaggctg   120
aggtcagtcg caggctggag aaccggctgg tgctgctgtt ctttggtgct ggggcttgtc   180
cacagtgcca ggccttcgtg cccatcctca aggacttctt cgtgcggctc acagatgagt   240
tctatgtact gcgggcggct cagctggccc tggtgtacgt gtcccaggac tccacggagg   300
agcagcagga cctgttcctc aaggacatgc caaagaaatg gctttttcctg cccttttgagg   360
atgatctgag gagggacctc gggcgccagt tctcagtgga gcgcctgccg gcggtcgtgg   420
tgctcaagcc ggacggggac gtgctcactc gcgacggcgc cgacgagatc cagcgcctgg   480
gcaccgcctg cttcgccaac tggcaggagg cggccgaggt gctggaccgc aacttccagc   540
tgccagagga cctggaggac caggagccac ggagcctcac cgagtgcctg cgccgccaca   600
agtaccgcgt ggaaaaggcg gcgcgaggcg gcgcgacccc ggggagggg ggtggggagg   660
agggcggggc cggggggctg ttctgacccg ctagggtgga ggagaggagt ggggtttgtt   720
gatgaacctc cacccccacc ccaccccgc acgcctgtaa tcccagcact ggggaggcc   780
aaggcgggag gatcgcttga gcccagaggt tcgagatcaa cctgggcaag agagtgagac   840
cctgactcta cgaaaattaa aagttagccc ggtgtggtgg cgcgcacctg tggcttagct   900
accctgaaaa aaaaaaaaaa aaaaaaaaa aaaaaaaaa aaaaaaa                   948
```